US009360367B2

(12) United States Patent
Day et al.

(10) Patent No.: US 9,360,367 B2
(45) Date of Patent: Jun. 7, 2016

(54) HANDHELD LIBS SPECTROMETER

(71) Applicant: SciAps, Inc., Woburn, MA (US)

(72) Inventors: David R. Day, Boxford, MA (US); Konstantin Derman, Somerville, MA (US); John Francis Egan, Middleton, MA (US); Paul Edward Soucy, Arlington, MA (US)

(73) Assignee: SciAps, Inc., Woburn, MA (US)

( * ) Notice: Subject to any disclaimer, the term of this patent is extended or adjusted under 35 U.S.C. 154(b) by 329 days.

(21) Appl. No.: 14/179,670

(22) Filed: Feb. 13, 2014

(65) Prior Publication Data
US 2014/0204377 A1 Jul. 24, 2014

Related U.S. Application Data

(63) Continuation-in-part of application No. 13/746,102, filed on Jan. 21, 2013.

(51) Int. Cl.
*G01J 3/30* (2006.01)
*G01J 3/443* (2006.01)
*G01J 3/28* (2006.01)
*G01N 21/71* (2006.01)
*G01J 3/02* (2006.01)

(52) U.S. Cl.
CPC .............. *G01J 3/443* (2013.01); *G01J 3/0272* (2013.01); *G01J 3/2823* (2013.01); *G01N 21/718* (2013.01); *G01N 2201/0221* (2013.01)

(58) Field of Classification Search
CPC .... G01N 21/718; G01J 3/0272; G01J 3/2823; G01J 3/443; G01J 1/0204
See application file for complete search history.

(56) References Cited

U.S. PATENT DOCUMENTS 3,760,144 A 9/1973 Herzberger
4,358,659 A 11/1982 Spohnheimer
(Continued)

FOREIGN PATENT DOCUMENTS

WO WO 2012/040769 A1 4/2012
WO WO 2012/135961 A1 10/2012
(Continued)

OTHER PUBLICATIONS

Written Opinion of the International Searching Authority for PCT Application No. PCT/US2014/12060 mailed Jan. 27, 2015 (five (5) pages).
(Continued)

*Primary Examiner* — Michael A Lyons
*Assistant Examiner* — Maurice Smith
(74) *Attorney, Agent, or Firm* — Iandiorio Teska & Coleman, LLP

(57) ABSTRACT

A handheld LIBS spectrometer includes an optics stage movably mounted to a housing and including a laser focusing lens and a detection lens. One or more motors advance and retract the optics stage, move the optics stage left and right, and/or move the optics stage up and down. A laser source in the housing is oriented to direct a laser beam to the laser focusing lens. A spectrometer subsystem in the housing is configured to receive electromagnetic radiation from the detection lens and to provide an output. A controller subsystem is responsive to the output of the spectrometer subsystem and is configured to control the laser source and motors. In this way, auto-calibration, auto-clean, and auto-focus, and/or moving spot functionality is possible.

77 Claims, 32 Drawing Sheets

(56) References Cited

U.S. PATENT DOCUMENTS

| | | |
|---|---|---|
| 5,473,162 A | 12/1995 | Busch et al. |
| 5,520,679 A | 5/1996 | Lin |
| 6,077,386 A | 6/2000 | Smith, Jr. et al. |
| 6,355,908 B1 | 3/2002 | Tatah et al. |
| 6,801,595 B2 | 10/2004 | Grodzins et al. |
| 7,233,643 B2 | 6/2007 | Spila et al. |
| 7,394,537 B1 | 7/2008 | Lindfors et al. |
| 8,184,287 B2 | 5/2012 | Hamilton et al. |
| 2001/0015801 A1 | 8/2001 | Hirose et al. |
| 2002/0009814 A1 | 1/2002 | Usui et al. |
| 2003/0010907 A1 | 1/2003 | Hayek et al. |
| 2003/0174325 A1 | 9/2003 | Zhang et al. |
| 2003/0234928 A1 | 12/2003 | Lucas et al. |
| 2004/0183010 A1 | 9/2004 | Reilly et al. |
| 2005/0056628 A1 | 3/2005 | Hu |
| 2005/0068524 A1 | 3/2005 | Wu et al. |
| 2005/0236563 A1 | 10/2005 | Busch et al. |
| 2005/0248758 A1 | 11/2005 | Carron et al. |
| 2006/0100676 A1 | 5/2006 | Walmsley |
| 2006/0262302 A1 | 11/2006 | Eklin |
| 2007/0187632 A1 | 8/2007 | Igarashi |
| 2007/0195311 A1 | 8/2007 | Morgan |
| 2007/0202613 A1 | 8/2007 | Usul |
| 2007/0265783 A1 | 11/2007 | Mound |
| 2008/0151241 A1 | 6/2008 | Lindfors et al. |
| 2008/0165344 A1 | 7/2008 | Treado et al. |
| 2008/0205755 A1 | 8/2008 | Jackson |
| 2008/0259330 A1 | 10/2008 | Dillon et al. |
| 2009/0007933 A1 | 1/2009 | Thomas et al. |
| 2009/0025761 A1 | 1/2009 | Matsumoto |
| 2009/0057422 A1 | 3/2009 | Dugas et al. |
| 2009/0103082 A1 | 4/2009 | Black et al. |
| 2010/0197116 A1 | 8/2010 | Shah et al. |
| 2011/0315661 A1 | 12/2011 | Morisawa |
| 2012/0029836 A1 | 2/2012 | Hermann |
| 2012/0044488 A1 | 2/2012 | Senac |
| 2012/0085366 A1 | 4/2012 | Hirota |
| 2012/0162642 A1 | 6/2012 | Watson et al. |
| 2012/0236303 A1 | 9/2012 | Marple et al. |
| 2012/0268743 A1 | 10/2012 | Wang et al. |
| 2012/0314214 A1 | 12/2012 | Alexander et al. |
| 2013/0016349 A1 | 1/2013 | Effenberger, Jr. et al. |
| 2013/0342902 A1 | 12/2013 | Krueger |
| 2014/0022531 A1 | 1/2014 | Sackett |
| 2014/0022532 A1 | 1/2014 | Sackett |
| 2014/0125965 A1 | 5/2014 | Nagli |
| 2014/0204378 A1 | 7/2014 | Day |

FOREIGN PATENT DOCUMENTS

| | | |
|---|---|---|
| WO | WO 2013083950 | 6/2013 |
| WO | WO 2015/057784 | 4/2015 |

OTHER PUBLICATIONS

Written Opinion of the International Searching Authority for PCT Application No. PCT/US2014/016188 mailed Feb. 2, 2015 (eight (8) pages).
U.S. Appl. No. 13/746,012, Day.
U.S. Appl. No. 13/746,095, Day.
U.S. Appl. No. 13/746,102, Day.
U.S. Appl. No. 13/746,108, Day.
U.S. Appl. No. 13/746,110, Day.
Written Opinion of the International Searching Authority for PCT Application No. PCT/US2014/11961 mailed May 8, 2014 (six (6) pages).
Written Opinion of the International Searching Authority for PCT Application No. PCT/US2014/11863 mailed May 13, 2014 (nine (9) pages).
Oxford Instruments, Laser Induced Breakdown Spectroscopy (LIBS), http://www.oxford-instruments.com/products/spectrometers/laser-induced-bre . . . , (two (2) pages).
Applied Spectra, Inc., Model RT100-EC, http://www.appliedsoectra.com/products/rt100-ec.html (four (4) pages).
RMG Technology Introduces Hand-Held Laser Analyzer, Recycling Today, http://www.recyclingtoday.com/Article.aspx?article_id=141665, (two (2) pages).
Ocean Optics, Laser-Induced Breakdown Spectroscopy, The LIBS2500plus LIBS Systems, http://www.oceanoptics.com/products/libs.asp, (four (4) pages).
Applied Photonics, LIBSCAN 25, brochure, (two (2) pages).

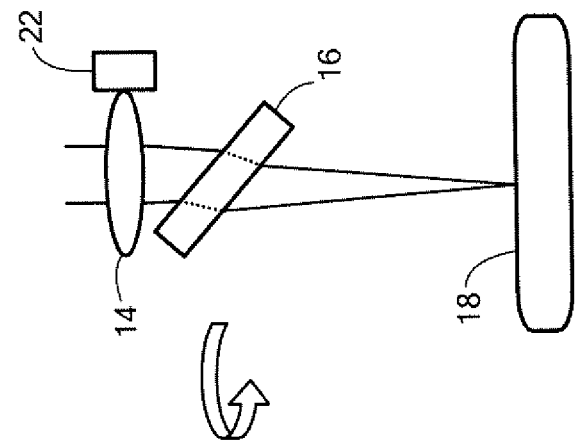
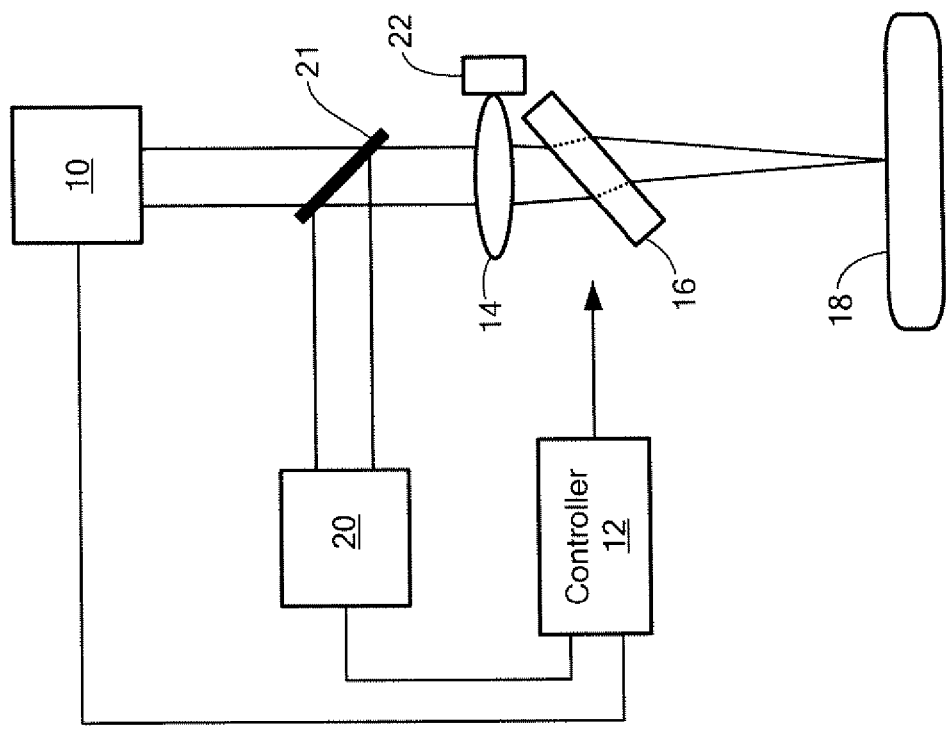

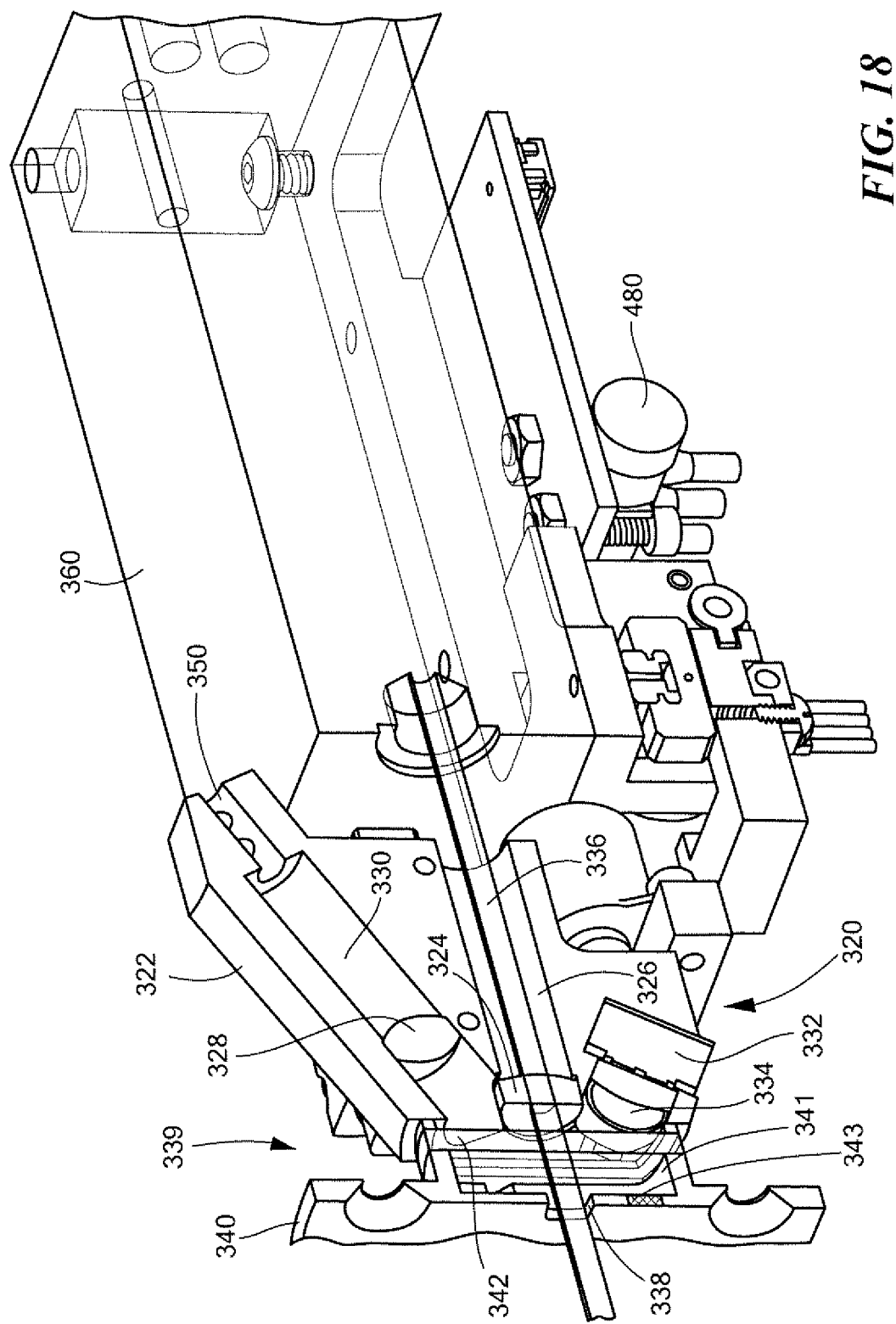

HANDHELD LIBS SPECTROMETER

RELATED APPLICATIONS

This application is a continuation-in-part application of U.S. patent application Ser. No. 13/746,102 filed Jan. 21, 2013 and claims the benefit of and priority thereto under 35 U.S.C. §§119, 120, 363, 365, and 37 C.F.R. §1.55 and §1.78 and is incorporated herein by this reference. This application is also related to application Ser. No. 13/746,110 filed Jan. 21, 2013; Ser. No. 13/746,095 filed Jan. 21, 2013; and Ser. No. 13/746,108 filed Jan. 21, 2013.

FIELD OF THE INVENTION

The subject invention relates to spectroscopic instruments.

BACKGROUND OF THE INVENTION

Various spectroscopic instruments are known. X-ray based instruments, for example, can be used to determine the elemental make up of a sample using x-ray florescence spectroscopy. Portable XRF has become a preferred technique for elemental analysis in the field. Portable XRF is fast, non-destructive, and provides reasonably accurate results (i.e., quantification of elemental concentrations in a wide variety of samples). With XRF, an x-ray tube is used to direct x-rays at a sample. Atoms in the sample absorb x-rays and re-emit x-rays that are unique to the atomic structure of a given element. A detector measures the energy of each x-ray and counts the total number of x-rays produced at a given energy. From this information, the types of elements and the concentration of each element can be deduced. Commercially available analyzers include the Delta manufactured by Olympus NDT and the Niton XLT-3 manufactured by Thermo Fisher Scientific.

X-rays, however, pose a safety concern. Also, portable and benchtop XRF analyzers have not to date been used to determine lower atomic number elements such as beryllium, sodium, carbon, boron, oxygen, nitrogen, lithium, and the like.

Laser induced break down spectroscopy (LIBS) devices are known and used to detect the elemental concentration of lower atomic numbered elements with some accuracy. These devices typically include a high powered laser that sufficiently heats a portion of the sample to produce a plasma. As the plasma cools, eventually the electrons return to their ground states. In the process, photons are emitted at wavelengths unique to the specific elements comprising the sample. The photon detection and subsequent measurement of elemental concentrations are similar to spark optical emission spectroscopy (OES). Examples of LIBS devices are the LIBS SCAN 25 from Applied Photonics, the LIBS25000 from Ocean Optics, and the RT 100 from Applied Spectra. See also Nos. US 201210044488 and WO 2013/083950 (PCT/GB20121000892) incorporated herein by this reference.

Some elements such as carbon, phosphorous, and sulfur react with oxygen resulting in a very low level signal which can be difficult to detect and/or properly analyze.

It is known to use an inert gas such as argon to purge the sample. Typically, the flow rate is high and the area purged is large. The gas may be used to purge a sample chamber in some prior art LIBS analysis systems. Accordingly, a large source (e.g., a tank) of argon gas is required and must be toted along in the field. Other analysis systems using an argon purge, such as a mobile spark OES analyzer, also use quite a lot of argon gas for purging.

SUMMARY OF THE INVENTION

In a LIBS device, it is desirable to use eye-safe lasers. One example of an eye-safe laser with enough power for LIBS usage are those at 1.5 micron wavelength. Other wavelengths are possible. Water absorbs heavily at this wavelength thus preventing the laser reaching the retina of the eye. Devices with eye-safe lasers receive a regulatory rating of either Class 1 or Class 2 depending upon the power level of the laser. Class 1 is the most desired because it is the least regulated. For handheld devices which operate in an open beam configuration, the Class 1 or Class 2 rating is highly desired because it yields the maximum operator safety and is subject to the least amount of regulation.

Because of the lower pulse energies currently available from 1.5 µm lasers, it is often necessary to focus the laser into a smaller spot size, typically 100 µm or less in order to get a high enough power density to ignite a plasma. Lower power lasers than are commonly used for bench top LIBS instruments are also desirable particularly in the case of a handheld or portable LIBS unit due to size and power restrictions imposed to maintain portability of the instrument. The very small beam spot size on the sample creates three problems that should be solved to make a LIBS device commercially viable. First, the laser must be focused precisely on the surface of the sample being analyzed for consistent analytical results. Second, the sample must be clean from surface contamination including oxidation on the same distance scale of 100 µm or less. Third, some samples are non-homogeneous. Thus, on a sample, locations even a small distance away from each other my yield different elements and/or different elemental concentrations. It is therefore desirable to design such a FIBS device to make several measurements at different regions of the sample and combine the results. The invention disclosed includes an eye-safe laser in one preferred embodiment. However, the invention is useful for lasers of other wavelengths and/or larger beam spots on the sample.

In one preferred example, a spectrometer system, preferably handheld or otherwise portable, is provided and is configured to automatically, based on spectral information, properly focus the laser on the sample, clean the sample, and analyze different locations on the sample.

In a portable, battery powered device, it is not desirable to require the user to carry a large tank of purge gas. In one preferred embodiment, a purge subsystem allows a small argon cartridge to be used (e.g., 3-6" long) because the purge gas is conserved. The flow rate during testing is low and the gas flow is directed only locally to the location on the sample where the plasma is generated by the laser beam. Moreover, the purge gas is supplied only just before testing and turned off at the end of a test (or even before). In this way, the purge gas is further conserved.

Featured is an analysis system comprising a laser source generating a laser beam for creating a plasma at a location on a sample and a spectrometer responsive to photons emitted by the sample at said location and having an output. A controller is responsive to a trigger signal and is configured to activate the laser source generating a series of laser pulses in a cleaning cycle, to process the spectrometer output, and to automatically terminate the cleaning cycle based on the spectrometer output.

Processing the spectrometer output may include analyzing the intensity of one or more peaks for multiple pulses. Terminating the cleaning mode may occur when said intensity changes by less than a predetermined percentage over a predetermined number of laser pulses. Analyzing the intensity may include computing a rolling average of the intensity over multiple pulses.

The system may further include an adjustable focusing lens for focusing the laser beam to a small spot size at the sample location. The controller can be configured to adjust the focusing lens to produce a larger spot size during the cleaning cycle.

A movable optic can be configured to sequentially create a plasma at multiple locations on the sample and the controller may be further configured to adjust the optic and to initiate and terminate the cleaning cycle at multiple locations on the sample.

Also featured is an analysis method comprising activating a laser source generating a series of laser pulses creating a plasma at a location on a sample in a cleaning cycle, detecting photons emitted by the sample at said location and producing an output, processing the output, and automatically terminating the cleaning cycle based on the output.

Featured is an analysis system comprising a moveable focusing lens, a laser having an output directed at the focusing lens, a spectrometer outputting intensity data from a sample. A controller system is responsive to the spectrometer and is configured to energize the laser, process the output of the spectrometer, and adjust the position of the focusing lens relative to the sample until the spectrometer output indicates a maximum or near maximum intensity resulting from a laser output focused to a spot on the sample. In this manner, an eye safe laser may be used.

In some embodiments, the detection path is through the focusing lens to the spectrometer. The laser output wavelength may be approximately 1.5 µm. The laser may be as low as class 1 laser with a focused spot size equal to or less than 100 µm on the sample.

The intensity is preferably an integrated intensity over a plurality of wavelengths. Adjusting the position of the focusing lens may include moving it away from the sample and towards the sample.

Also featured in some example is a moveable optic configured to direct focused laser energy to multiple locations on the sample. The controller system may further be configured to initiate a moving spot cycle wherein the orientation of the moveable optic is adjusted and again the laser is energized and the output of the spectrometer processed. The controller system may be configured to terminate the moving spot cycle when the spectrometer output does not change by a predetermined amount between different sample locations. Preferably, the controller system is configured to adjust the position of the focusing lens at each sample location. In one example, the movable optic includes the focusing lens. In other examples, the movable optic includes one or more mirrors or a glass optic.

In some examples, the controller system may be configured to initiate a cleaning cycle and to terminate the cleaning cycle—processing the spectrometer output and energizing the laser in a cleaning mode until the output stabilizes. The cleaning cycle may automatically terminate when a rolling average of at least one peak intensity changes by less than a predetermined percentage. The controller can be configured to move the position of the focusing lens producing a larger spot size during the cleaning cycle and to return the focusing lens to a focused position after terminating the cleaning cycle Also featured is an analysis system comprising an adjustable focusing lens, a laser having an output directed at the focusing lens, a moveable component configured to direct laser energy to multiple locations on a sample, and a spectrometer outputting intensity data from the sample. A controller system is responsive to the spectrometer and is configured to initiate a focusing cycle wherein the laser is energized, the spectrometer output is analyzed, and the position of the focusing lens is adjusted until the spectrometer output is optimized resulting from a laser output focused on the sample. The system initiates a cleaning cycle wherein the laser is energized, the spectrometer output is analyzed, and the cleaning cycle terminates when the spectrometer output stabilizes. The system initiates a moving spot cycle wherein the movable component is adjusted and the spectrometer output is analyzed for multiple locations on the sample.

Also featured is an analysis method comprising energizing a laser producing a beam impinging on a sample, analyzing the resulting photons, and based on the analysis, automatically adjusting the focus of the laser beam on the sample to produce a focused spot on the sample. The focus of the laser beam may be adjusted until a maximum or near maximum intensity is reached at one or more wavelengths. Photons may be directed from the sample along a detection path through the focusing lens to a detector system.

The method may further include cleaning the sample using the laser beam. Cleaning can include adjusting the focus of the laser to produce a larger spot. Cleaning the sample may include energizing the laser, analyzing the resulting photons, and terminating cleaning when an intensity stabilizes.

One method may include moving the beam to multiple locations on the sample and optionally adjusting the focus of the laser beam at each location. The method may include cleaning the sample at each location using the beam. The beam can be moved until analysis of the sample indicates a homogeneous sample. For a non-homogeneous sample, the beam may be moved a predetermined maximum number of times.

Also featured is a spectroanalysis method comprising directing a laser output at an adjustable focusing lens, detecting intensity data from the sample, and initiating a focusing cycle wherein the laser is energized, the intensity data is analyzed, and the position of the focusing lens is adjusted until the intensity data is optimized resulting in a laser output focused on the sample. A cleaning cycle is initiated wherein the laser is energized, the intensity data is analyzed, and the cleaning cycle terminates when the intensity data stabilizes. A moving spot cycle is initiated wherein the laser output is moved to a new location on the sample and the intensity data is analyzed for multiple locations on the sample.

In some examples, the focusing lens may be adjusted to make the predetermined spot larger during the cleaning cycle. The focusing cycle and cleaning cycle may be initiated for each location on the sample during the moving spot cycle. In one example, the moving spot cycle terminates when the intensity data indicates the sample is homogeneous.

Featured is a handheld LIBS spectrometer comprising an optics stage movably mounted to a housing and including a laser focusing lens and a detection lens. One or more motors advance and retract the optics stage, move the optics stage left and right, and/or move the optics stage up and down. A laser source in the housing is oriented to direct a laser beam to the laser focusing lens. A spectrometer subsystem in the housing is configured to receive electromagnetic radiation from the detection lens and to provide an output. A controller subsystem is responsive to the output of the spectrometer subsystem and is configured to control the laser source and the motors. The optics stage may further include a camera with a camera lens.

In one design, one or more rails are attached to one of the optic stage and the housing and corresponding one or more linear bearings are attached to the other of the optics stage and the housing. The motors are attached to one of the optic stage and the housing to drive the other of the optics stage and the housing for moving the optic stage relative to the housing. Preferably, the optic stage includes an optics head with the laser focusing lens and detection lens. In one design, a first frame member is moveably coupled to the housing in a first direction and a second frame member is moveably coupled to the first frame member in a second direction and moveably coupled to the optics head in a third direction. A first motor drive drives the first frame ember relative to the housing in the first direction, a second motor drive drives the second frame member relative to the first frame in the second direction, and a third motor drive drives the optics head relative to the second frame in the third direction. The first motor drive may move the optics head right and left, the second motor drive may move the optics head up and down, and the third motor drive may move the optics head forward and rearward.

In one embodiment, the controller subsystem is configured to control these motors to move the optics stage to initiate a calibration routine. One calibration routine may include computer instructions which control the motors to move the optics stage to a predetermined set of coordinates, to power the laser to produce a laser beam, to process the output of the spectrometer subsystem, and to calibrate the spectrometer. The computer instructions which calibrate the spectrometer may include instructions which determine wavelength and/or intensity calibration constants based on the output of the spectrometer subsystem. Preferably the controller subsystem is configured to control the motors to move the optics stage to initiate an auto-focus routine, and auto-clean routine, a moving spot cycle, and/or a purge cycle.

The moving spot cycle may include computer instructions which control the motors to move the optics stage to a plurality of locations and, at each location, to power the laser to produce a laser beam and process the output of the spectrometer subsystem. The controller subsystem may be configured to initiate the auto-focus routine and the auto-clean routine at each location on the sample. The controller subsystem may be configured to initiate the purge cycle during the moving spot cycle.

In one design, the laser source has an output wavelength of approximately 1.5μ and the laser source is a class one or class two laser. The laser focusing lens may be configured to produce a laser spot size equal to or less than 100μ on a sample.

In some designs, the spectrometer subsystem includes a plurality of optical bundles optically coupled between the detection lens and a plurality of spectrometer enclosures. The spectrometer enclosures may be coupled to each other in the housing. Preferably, each spectrometer enclosure includes a floor and an open top, and the floor of one enclosure is configured to cover the open top of an adjacent enclosure. The outer spectrometer enclosure in the array may include a lid covering its open top. Each spectrometer enclosure may include optical devices directing electromagnetic radiation from its optical bundle to a sensor (e.g., a CCD sensor). Preferably, the optical devices are adjustable with respect to the spectrometer enclosure. The optical devices may include a grating with different spectrometer enclosures having different gratings and/or gratings at different angles. The optical devices of each spectrometer enclosure may be in a Czerny-Turner configuration.

The handheld LIBS spectrometer may include a nose section forward of the optics stage and attached to the housing. In one design, the nose section includes an end plate with an aperture for the laser beam passing through the laser focusing lens. The nose section may also include a shield spaced from the end plate defined defining a purge cavity between the shield and the end plate in front of the optics stage. The shield may be made of fused silica for protecting the laser focusing lens and detection lens of the optic stage from plasma generated by the laser.

The handheld LIBS spectrometer may further include a gas source fluidly coupled to the purge cavity. In one design, the housing includes a handle and the gas source includes a gas cartridge pivotably disposed in the housing handle. Preferably, the gas source cartridge is fluidly coupled to the purge cavity via a regulator, the regulator is rotatably coupled to the housing, and the gas source cartridge is coupled to the rotating regulator.

The gas source may be fluidly connected to the purge cavity via a controllable valve and the controller subsystem is configured to automatically control this valve.

In some designs, the nose section includes an on-board calibration standard for self-calibrating the spectrometer when controller subsystem controls the optic stage to orient the laser focusing lens to focus laser energy on the calibration standard of the nose section.

Also featured is a handheld LIBS spectrometer comprising a housing, an optics stage movably mounted to the housing, a laser source in the housing oriented to direct a laser beam to the optics stage, and a spectrometer subsystem in the housing configured to receive electromagnetic radiation from the optics stage and provide an output. The spectrometer subsystem includes a plurality of stacked spectrometer enclosures.

Also featured is a handheld LIBS spectrometer comprising a housing, an optics stage movably mounted to the housing including an optics head with a laser focusing lens and a detection lens, a laser source in the housing oriented to direct a laser beam to the laser focusing lens, a spectrometer subsystem in the housing configured to receive electromagnetic radiation from the detection lens and provide an output, and a nose section including an end plate and a removable shield spaced from the end plate and in front of the optics head defining a purge cavity between the shield and the end plate. Preferably, the end plate is made of or includes a portion made of a calibration standard.

Also featured is a method of analyzing a sample using a handheld LIBS spectrometer. A laser is powered to produce a laser beam spot on a sample. Preferably a controller initiates an auto-focus cycle to focus the spot on the sample, initiates an auto-clean cycle to clean multiple locations on the sample, and initiates a moving spot cycle to analyze the sample.

The auto-focus cycle may include retracting and advancing a laser focusing lens, powering the laser, and analyzing a spectrum until the spectrum indicates a maximum or near maximum intensity resulting from a laser output focused to a spot on the sample. The auto-clean cycle may include powering the laser, analyzing a spectrum, and moving the laser beam about the sample until the spectrum output stabilizes. The auto-clean cycle may automatically terminate when a rolling average of at least one peak intensity changes by less than a predetermined percentage. During the moving spot cycle, the laser is powered, a spectrum data is analyzed, and the laser beam spot on the sample is moved.

The method may further include automatically initiating an auto-calibration cycle. In one example, during the auto-calibration cycle the laser beam is aimed at a calibration standard, the laser is powered to produce a laser beam focused at the standard, a spectrometer output is analyzed, and calibration constants are determined.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features, and advantages will occur to those skilled in the art from the following description of a preferred embodiment and the accompanying drawings, in which:

FIGS. 3A and 3B are block diagrams showing still another example of a spectrometer system in accordance with the invention;

FIG. 18 is a schematic three dimensional front view of the movable optics head of the system of FIG. 17;

DETAILED DESCRIPTION OF THE INVENTION

Figure 1:
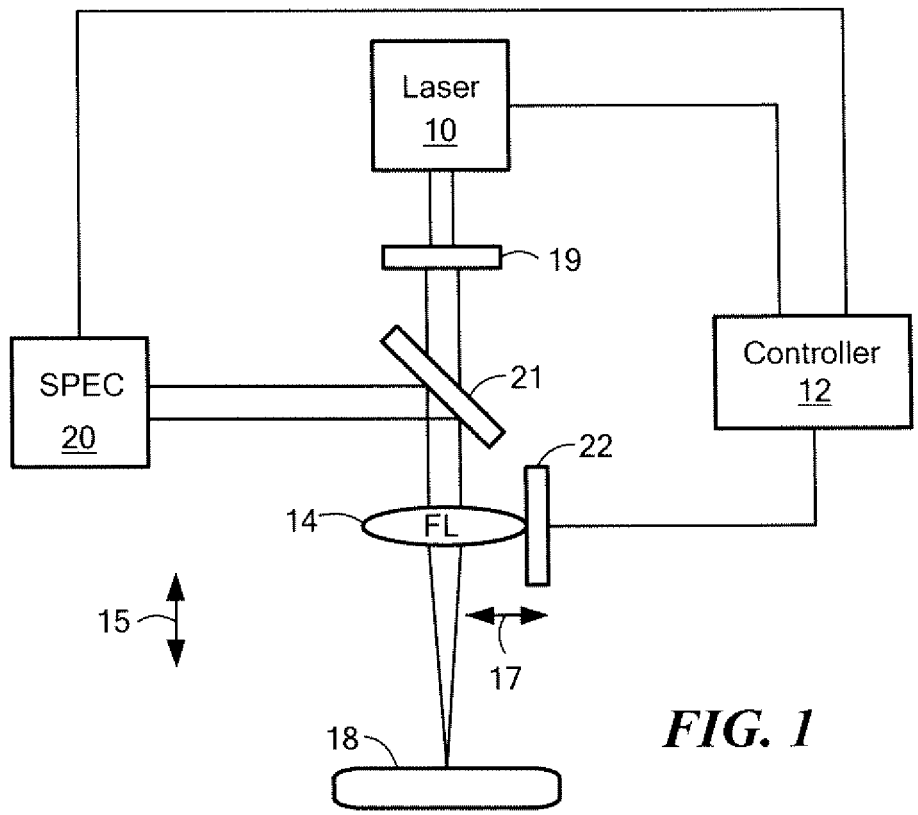
FIG. 1 is a block diagram showing an example of a spectrometer system in accordance with the invention.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

In the example of FIG. 1, a LIBS laser 10 directs its collimated output, when energized by controller subsystem 12, to adjustable focusing lens 14 which produces a small spot (e.g., 100 µm) of laser energy on sample 18 creating a plasma. The focusing lens can be moved in the axial direction, meaning in a direction perpendicular to the surface either closer to or further from the sample as shown by arrow 15.

The resulting photons of the plasma produced by the laser energy proceed along a detection path including focusing lens 14 to subsystem 20 (e.g., a spectrometer). The output signal of detector subsystem 20 may be processed by controller subsystem 12. In this particular example, high pass filter 21 passes laser energy (e.g., at, for example, 1500 nm) from LIBS laser 10 to lens 14 and reflects lower wavelengths (e.g., below about 1,000 nm) to subsystem 20 which may include a slit.

A translation mechanism 22 may be provided under the control of controller subsystem 12 to move focusing lens 14 in the axial direction towards or away from the sample surface (vertically in the figure) in order to permit focusing control for rough sample surfaces as well as to compensate for any path length variations introduced by the optics. A stepper motor combined with gears and the like can be used to adjust the position of focusing lens 14. An electromagnetic coil or other means of translation may also be used.

Spectrometer 20 may include a CCD detector array as set forth in the design of co-pending application Ser. Nos. 13/591,907 and 13/507,654 incorporated herein by this reference. Other spectrometers include echelle (with a 2D CCD), Paschen-Runge, and the like.

Controller subsystem 12 may include one or more microprocessors, digital signal processors, analog and/or digital circuitry or similar components, and/or application specific integrated circuit devices and may be distributed (e.g., one micro-processor can be associated with the detector subsystem while a micro-controller can be associated with the device's electronic circuit board(s). The same is true with respect to the algorithms, software, firmware, and the like. Various electronic signal processing and/or conditioning and/ or triggering circuitry and chip sets are not depicted in the figures. Additional optics including beam expansion, collimation, and/or adjustment optics are possible in some examples. Beam expansion optic 19 is shown for increasing the diameter of the laser output impinging on focusing lens 14. Laser 10 is preferably a class 1 eye safe laser.

Mechanism 22 may also be configured to move focusing lens 14 right and left in the figure as shown by arrow 17 (and/or in a direction in and out of the plane of FIG. 1) to move the laser beam spot to multiple locations on the sample. In one example, controller 12 is configured to automatically focus the laser beam on the sample, clean the sample, analyze the sample, and then move the laser beam and again properly focus the beam, clean the new location, and again analyze the sample. These features are discussed below.

Figure 2:
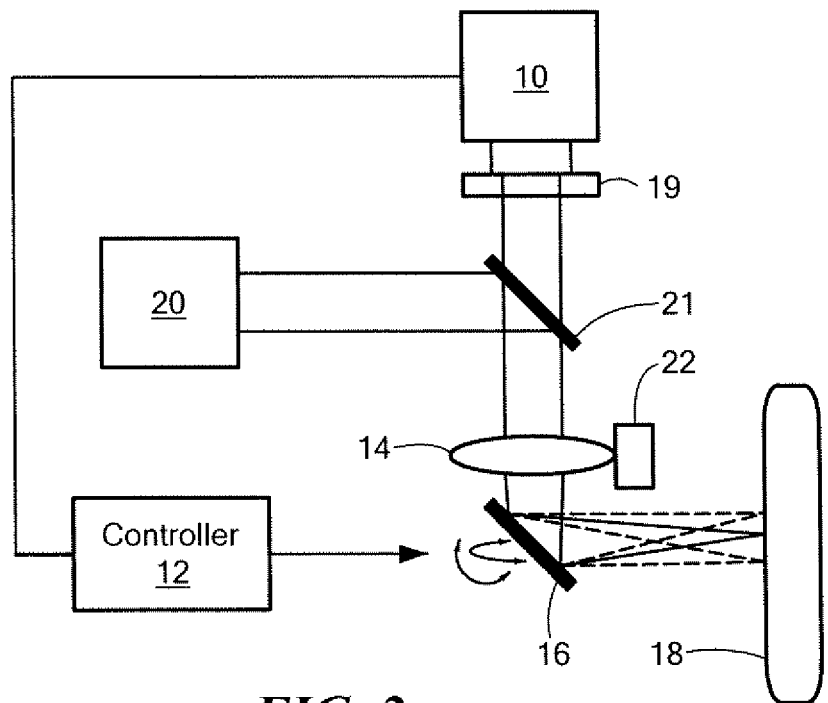
FIG. 2 is a block diagram showing another example of a spectrometer system in accordance with the invention.

Another way to move the laser beam to multiple locations on the sample is to use adjustable optic 16, FIG. 2. Optic 16 may include a tip-tilt mirror electromagnetically or electrostatically driven, MEMS mirrors, and the like such as those available from Mirrorcle Technologies, Thor Labs, Newport, as well as other suppliers.

In FIG. 3, the delivery and return optical paths are similar to those described for FIG. 1. This example includes a rotating glass window (optic 16) as an alternative method for implementing spot translation on the sample. The change in refractive index between free space and the glass window combined with the angle of the glass window relative to the optical axis results in a lateral shift of the laser beam as shown in FIGS. 3A and 3B. Rotating the glass around a glass optic 5 mm thick with a refractive index of 1.5 for example, may be used. If the glass surface is angled at 55° to the optical axis, the lateral displacement would be approximately 2.2 mm. By rotating the glass optic around the optical axis as shown in FIGS. 3A and 3B, the focus spot would follow a circle of radius 2.2 mm on the sample surface (e.g., a circle circumference of approximately 14 mm). If the glass optic is rotated about the optical axis in 6 degree steps, measurements of 60 unique areas of the sample are enabled each separated by about 0.23 mm.

Another version could include two sequential rotating glass optics, similar to the single optic shown in FIGS. 3A and 3B allowing full translational control in the X and Y directions on the sample rather than just being limited to a circle. In still other designs, a composite glass translation optic could be used to reduce or eliminate refractive index dispersion effects which might result in small differences in translation verses wavelength.

One of the advantages of the geometries of FIGS. 1, 2 and 3 is that the LIBS laser and the optical emission detection optics of the detector subsystem stay aligned on the same sample point as the sample location is modified by the movable optic.

Controller subsystem 12 is typically configured (e.g., programmed) to energize (e.g., pulse) the laser producing a series of laser pulses and to analyze the sample at one location by processing the output of the spectrometer between pulses. The controller subsystem is typically configured to receive a trigger signal (generated by the operator pushing a physical or virtual button or the like) and in response to pulse the laser. The controller subsystem then adjusts the movable optic (14, FIG. 1; 16, FIGS. 2-3) and again energizes the laser and analyzes the sample now at a different location. A typical controller subsystem of a hand held or portable device will typically display, on an output screen, the elements detected and, optionally, their concentrations.

Operating the laser in the "eye safe" wavelength range of 1.5 μm offers significant advantages to handheld LIBS analyzers. Handheld units are by design open beam meaning the laser beam exits the unit before striking the sample. Therefore, scattered laser light (or direct laser light in the case of extreme misuse) could strike the user's eye. However because laser light at this wavelength is strongly absorbed by water, the laser light cannot reach the retina. The laser is therefore rated as either as low as Class 1 depending on total energy. A Class 1 rating in particular is a significant commercial advantage as it eliminates the requirement of special safety glasses be worn during usage and regulatory requirements are greatly reduced compared to the most regulated Class 4 type of lasers. An eye safe laser may be preferred (e.g., class 1 or 2) and a safer laser source can be used in some embodiments (e.g., class 3) with the understanding that the class of laser and safe rating depends on variables such as energy level, wavelength, pulse width, pulse rate, divergence angle, and the like.

However, lasers that operate in the "eye safe" wavelength range near 1.5 μm create a number of hurdles, addressed below, that are needed to make this type of laser practical.

The LIBS technique requires that a burst of laser light strikes a sample, and deposits enough heat in the area struck so as to generate a plasma. When the plasma cools, electrons from the various elements that comprise the sample fall from various excited states to lower energy states, emitting photons in the process. The frequency of the emitted photon is proportional to the energy of the photon which is, in turn, equal to the difference between the two energy states. The frequency (or its inverse, wavelength) and intensity of the photons are measured by a spectrometer type detector to determine chemical composition of the sample spot where the plasma was created.

Portable or handheld LIBS systems are designed to operate from batteries and therefore are limited in power. If a portable or handheld LIBS system also uses an eye-safe laser, the energy available in the laser, at least with currently available technology, is further reduced. In order to generate a sufficient energy density for plasma ignition in the sample region being analyzed under these conditions, the laser is preferably focused down to a much smaller spot size than required for higher power bench top lasers, e.g., on the order of 5 μm-100 μm by lens 14, FIGS. 1-3. The initiation of a plasma is dependent mainly on power density rather than total power. Therefore, a lower power laser must be focused to a smaller spot size to attain sufficient power density for plasma ignition. It is therefore possible to use a much lower powered laser that is more conducive to a handheld or portable LIBS unit and yet still generate a plasma on the sample surface. The main trade-off of lower power lasers is that the ablation area on the sample will be reduced in area resulting in a more localized measurement and a lower signal.

A small sample area (5 μm-100 μm in diameter) does however create problems that should be solved to use a portable or handheld LIBS device for real-world applications. First, it can be important that the laser be focused at the location where the analysis is required. For most samples, this is the surface of the sample. A small deviation in the focus position for whatever reason means the laser is focused slightly above the sample surface, yielding incomplete plasma formation, or the laser light strikes the surface before reaching the focal point (which theoretically is at some depth inside the sample in this case). In either case, an incomplete plasma is formed with poorer light formation or the plasma is not representative of the sample being tested leading to erroneous analytical results. Also, in many real-world cases, samples being tested are not completely smooth or they are not flat (such as wires, tubes, rods, etc.). In these cases the ideal focus may vary from sample to sample such as testing a flat piece of steel followed by testing a ¼" diameter steel rod or a ⅛" welding rod or wire. Adjustable focusing lens 14, FIGS. 1-3 under the control of controller 12 also allows for proper focusing in samples with features which block or interfere with the head of the portable device.

The second issue is sample cleanliness. LIBS is a very sensitive technique and the depth of the region being analyzed is typically just several microns, coupled with a sample area diameter of 5-100 μm. It is therefore important that the surface being analyzed is representative of the sample and is therefore free of dirt, oils, and/or oxidation. Prior to taking spectral data to determine composition, it is typical to fire a number of "cleaning shots" with the laser. These cleaning shots burn off material on the surface allowing underlying clean material to be analyzed. However, as stated above in order for the cleaning tests to be effective, the laser must be properly focused as well. In battery powered devices, it is important not to fire cleaning shots which are not required in order to conserve both battery power and analysis time.

A third issue is sample inhomogeneity. For certain types of samples such as vacuum melt alloys, the samples are likely very homogeneous over a 50 μm-100 μm laser beam spot size. However for geochemical samples (soils, sediments, ores) or liquid suspensions (as a few examples), it is likely that the concentration of the sample changes over a 5 μm-100 μm sample area. Therefore, it can be important to fire the laser at several different locations on the surface of the sample and to average the results.

Figure 4A:
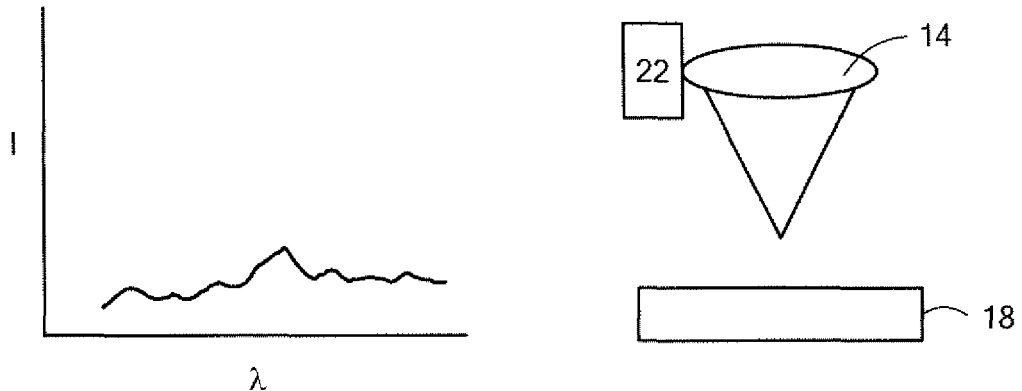
FIGS. 4A-4C are schematic views showing sample spectral intensity data as determined by a detector subsystem in accordance with FIGS. 1-3 at three different focusing lens positions for a technique used to determine the optimal focusing lens position in accordance with examples of the invention.

In embodiments of the invention, translating mechanism 22, FIG. 1-3 moves the focusing lens 12. At the first scan location, the laser is fired and a spectrum from the sample is acquired. A typical spectrum that shows intensity of light measured versus wavelength is shown in FIG. 4. The entire spectrum or one or more regions of the spectrum as output by the spectrometer are integrated by the controller 12, FIGS. 1-3. The lens 14 is then moved incrementally through a series of positions causing the laser focus to occur in front of the sample and then progressing into the sample bulk. Intensity data is gathered and stored for each focus position. The lens may be moved from a furthest away position to a closest position (a typical range of about 6 mm) in 0.01-1 mm increments.

Figure 4B:
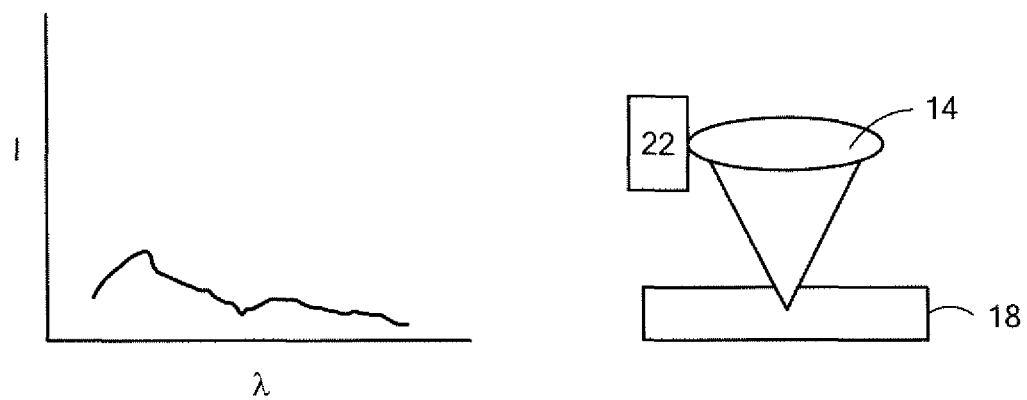
Figure 4C:
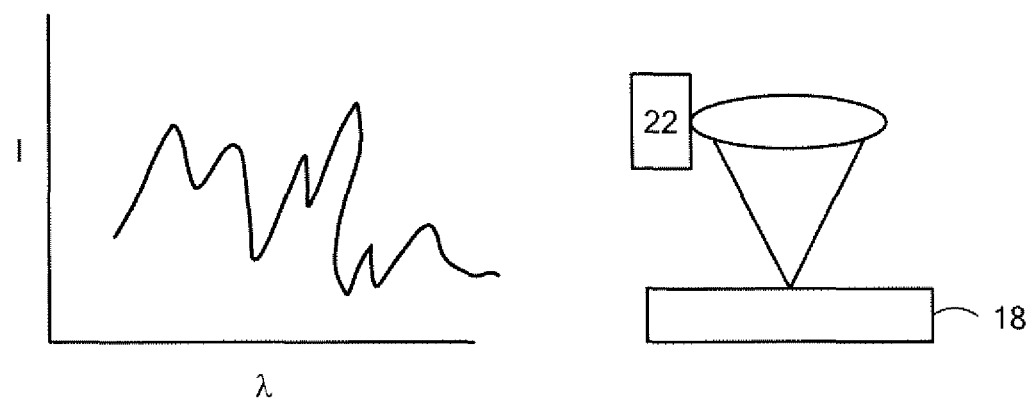

FIG. 4 shows the intensity data where lens 14 is too far away from sample 18; FIG. 4B shows the intensity data where lens 14 is too close to sample 18; and FIG. 4C shows the intensity data when the lens 14 is producing a preferred, optimum spot size (e.g., 50-100 μm) on the surface of sample 18. In FIG. 4C, the intensity is at a maximum. Controller 12, FIGS. 1-3, is programmed to detect a maximum or near maximum intensity by adjusting the lens focus from outside to inside the sample. The information is then available to the controller on where the lens should be positioned for both large cleaning pulse spots and smaller spots to be used for data collection.

Figure 5:
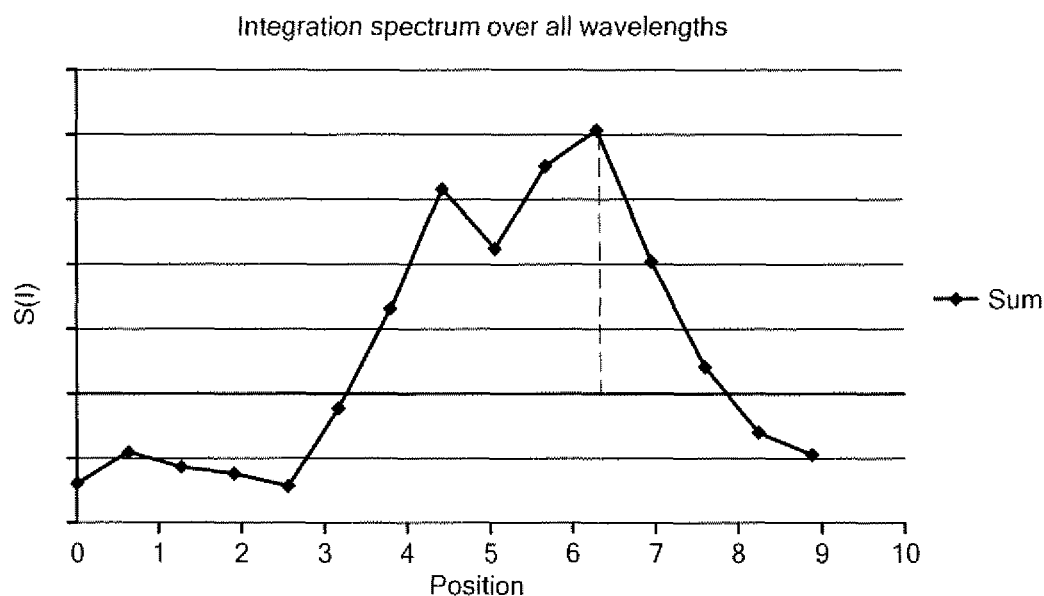
FIG. 5 is a graph showing the integration of spectral intensity over all wavelengths for ten different focusing lens positions.

An example of data from a carbon steel sample is shown in FIG. 5. The integrated intensity will approach a peak value at the correct optimal focal location as shown for position 6 in FIG. 4. For the data shown, the increments were in steps of 600 μm movement for the focusing lens, although the step size can be made smaller. Therefore, when a sample is placed in front of the device, the first step is that spectra are gathered at several focusing lens locations in order to automatically fine tune the focal spot of the laser on the sample. Controller 12, FIGS. 1-3 is configured to perform these steps as part of the initial testing and to determine and save the focusing lens location that yielded the maximum intensity. After the optimal focusing position is determined automatically, the processor moves the lens to this location and may then begin testing the sample or optionally, moves the lens to create a larger than optimum spot size for the purposes of cleaning, followed by data collection at the optimum (smallest) spot size. The controller is preferably configured to perform this task automatically rather than requiring operator input and judgment.

Without a process to automatically focus the laser onto the sample, the operator may not know if the sample results were correct. The concentration results determined by the instrument are related to the intensity of light measured in specific regions of the spectrum. If the laser is not properly focused, the concentration results will be inaccurate. For a commercially viable product, it is desirable that the instrument automatically determine the correct focusing location for the laser. Otherwise, an operator would have to manually perform measurements to make this determination. This may require a far higher skill level operator and therefore could diminish the commercial success of the LIBS device.

A next step in the analysis is to automatically determine if the sample location being tested is sufficiently clean. One cleaning cycle method is to take multiple repeat laser tests of the area and identify two (typically) of the largest spectra (atomic emission) peaks using available peak finding algorithms. Smaller peaks may also be selected that are important to the analysis at hand. These peaks correspond to particular elements present in the sample area being tested. Additional laser tests of the sample area are performed. Controller 12 then computes a rolling average of the intensity measured for the above two elements. When the intensity stops changing by less than a predetermined percentage from each point in the rolling average (for example by less than 5%), then the sample is appropriately cleaned. An alternative method for determination of cleanliness would be to compute the intensity ratios of the rolling averages. Once the ratio stabilizes to within a preset percentage, the sample may be considered to be clean.

Figure 6A:
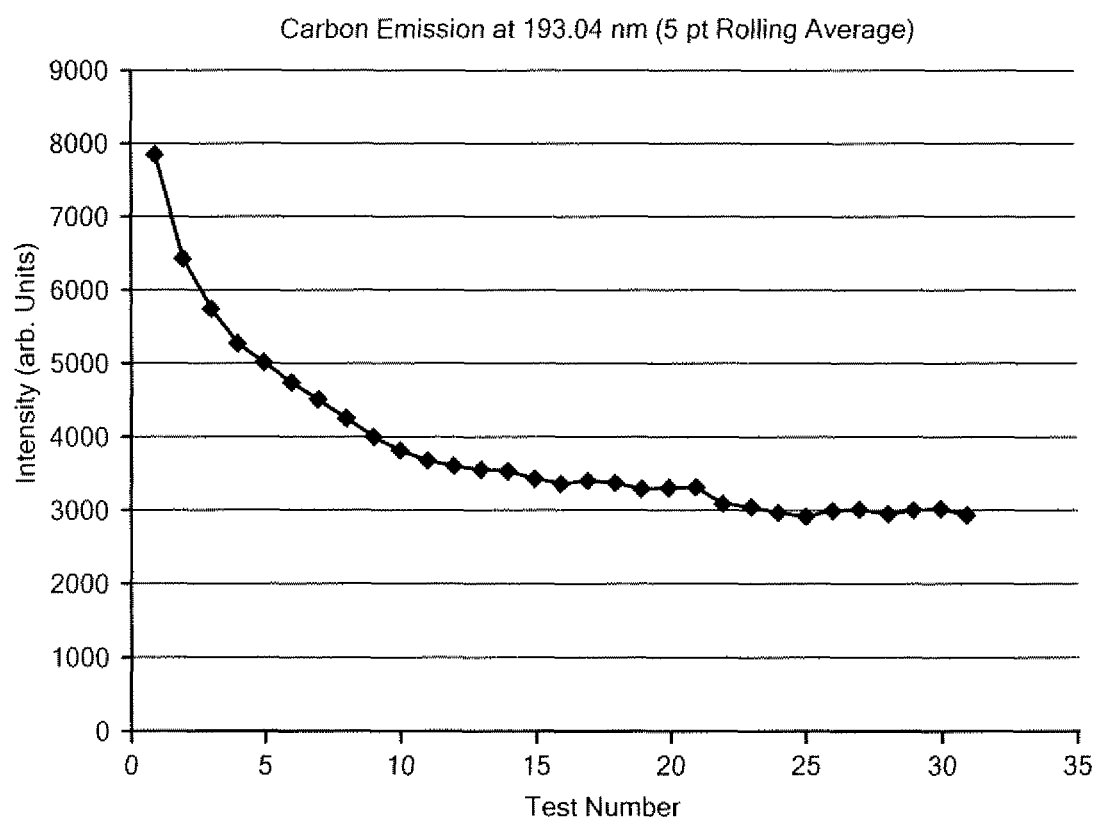
FIG. 6A is a graph showing intensity for carbon in a steel sample during sequential laser pulses in accordance with a cleaning method associated with embodiments of the invention.
Figure 6B:
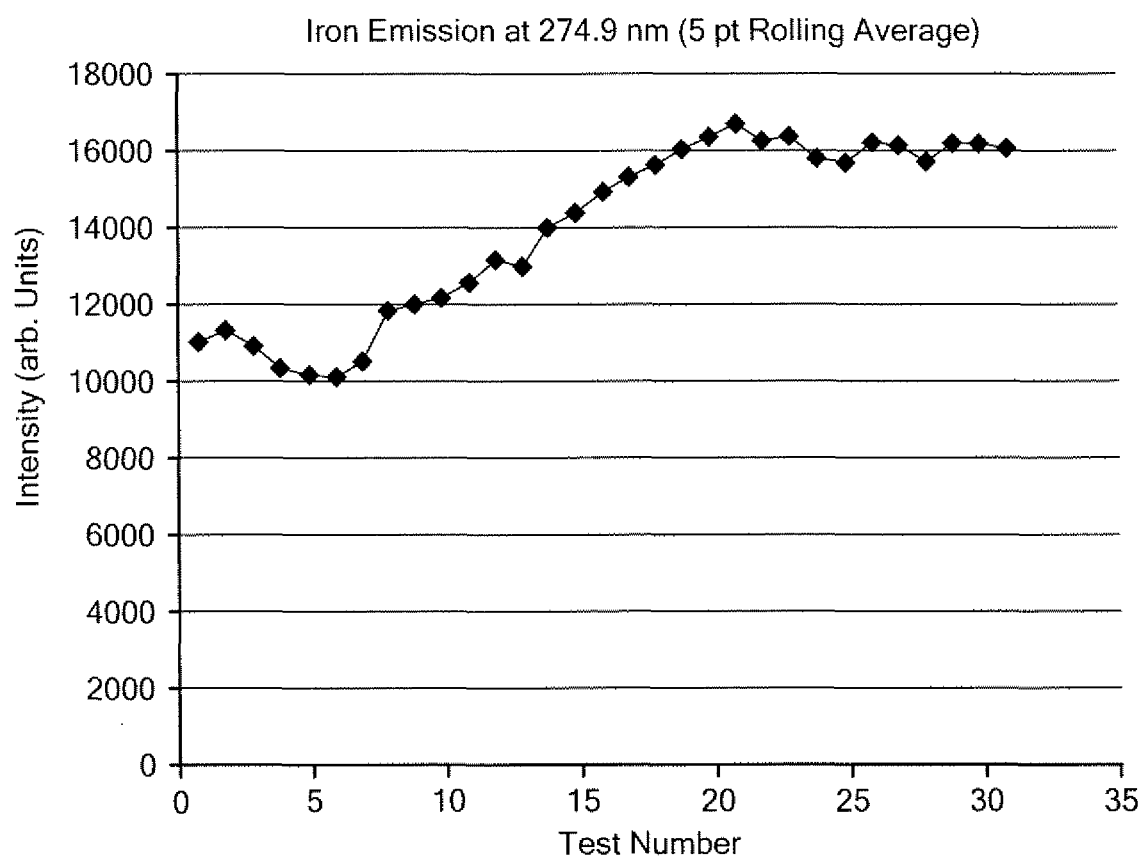
FIG. 6B is a graph showing intensity for iron during sequential laser pulses in accordance with the cleaning method associated with FIG. 6A.
Figure 7A:
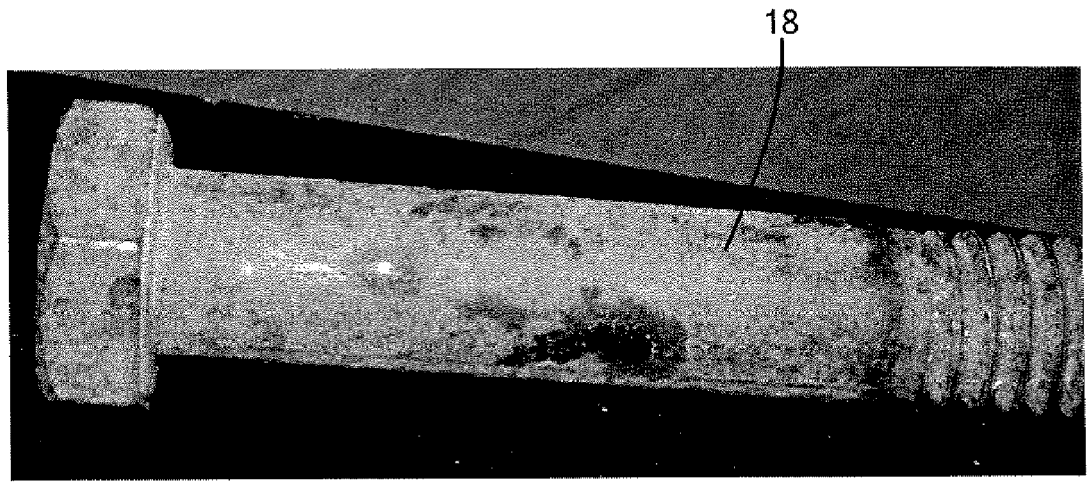
FIG. 7A is a view of a sample to be cleaned by the LIBS laser of FIGS. 1-3 prior to performing an analysis.

An example of peak intensity verses cleaning pulse count is shown in FIGS. 6A and 6B for a sample of rusty carbon steel (photo in FIG. 7). The cleaning cycle requires that a layer of dirt and oxidation be burned off by the laser blasts. As shown, the intensity of the carbon peak (FIG. 6A) and iron peak (FIG. 6B) change with sequential tests (laser pulses) until the results approach a stable intensity level. Here, 25 laser pulses resulted in a stabilized detector output. The method in this case may use a five point moving average. The carbon intensity (FIG. 6A) decreases with the sequential cleaning tests as carbon-containing organic material (i.e. dirt, oils, or skin oils) are burned of the sample. The point at which the carbon intensities stop decreasing indicate that only the base metal is being tested.

Likewise, the iron concentration (FIG. 6B) increases during the early cleaning tests as oxidation and other materials are burned off which were masking the iron content in the sample. Again, as the change in intensity of the iron photon emissions flatten with increasing test number, the base iron in the sample is being analyzed.

In principle, it may possible to only use a single peak for the automatic determination of when to end the cleaning tests. In addition, when testing for low concentrations of an element, say 1% carbon in 99% iron, the carbon line will be far more sensitive to cleanliness than the iron since the ratio of contamination to sample carbon is large and the ratio of contamination to iron is small. The peaks which are selected for analysis may include typical elements in the bulk sample or in the contamination coating such as carbon, oxygen, and silicon. By automatically stopping the cleaning cycle when the sample is sufficiently clean, battery power is conserved and testing time is reduced. It should be noted that the process of finding the optimal focal length for the sample, described above, also provides some cleaning of the sample spot, thereby reducing the number of cleaning tests performed in this step.

Figure 7B:
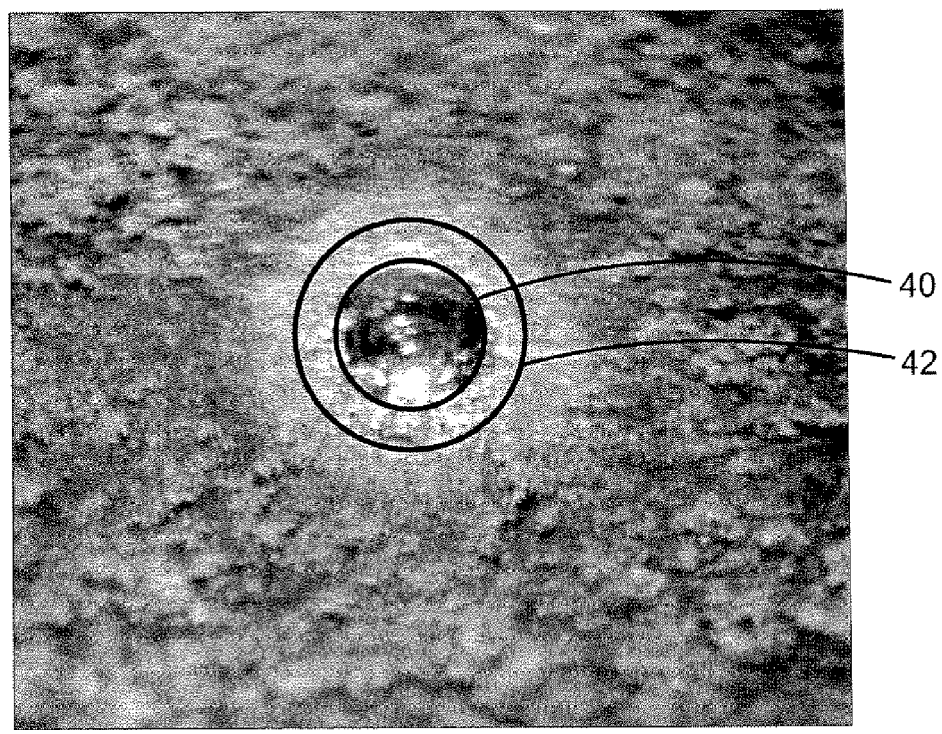
FIG. 7B is a view of a portion of the sample of FIG. 7A after cleaning.

One preferred cleaning method also results in an optimal manner to perform the cleaning and the subsequent sample analysis. Based on the testing performed to develop this method, a number of observations were made about the sample cleaning. Consider the pictures of a sample shown in FIGS. 7A and 7B. Upon examination of the area struck by laser, it was observed that the inner portion of the circular laser spot area 40, FIG. 7B, is well-cleaned but near the perimeter 42 of the analysis area, the cleaning may be less thorough.

In the real world of non-ideal lenses, lasers, and diffraction limited optics, it is expected that the inner component of the laser beam will deliver more energy to the sample than the outer perimeter of the beam. The region of the sample will thus be better cleaned more towards the center of the sample area. Therefore, an additional embodiment of the cleaning cycle method is to clean a larger area, in one example, than is actually analyzed. After the controller determines the optimal laser beam focal length as described previously, the focusing lens is moved such that the beam striking the sample surface during cleaning tests is about 20% larger. See, e.g., FIG. 4B. When the controller determines that the sample region is adequately cleaned, according to the above described steps, then the controller returns the focusing lens to the optimal position previously determined and stored. This assures that the area struck by the laser during analysis is therefore smaller than the area cleaned assuring that the area to be analyzed is thoroughly cleaned.

Another problem addressed is sample non-homogeneity. Many samples, for example geochemical samples encountered in the analysis of soil, ores, sediments and/or slurries are not homogeneous across the sample face. In other techniques, such as x-ray fluorescence analysis, the samples are collected and ground to about a 100 µm particle size prior to analysis. However, 100 µm is approximately the same size as the laser beam on the sample in the case of a LIBS analysis in accordance with embodiments of the invention. It is therefore desirable to test multiple locations on the sample and average the results.

The method provides for an optical/mechanical means which moves the laser beam spot across the sample as discussed with respect to FIGS. 1-3 to address the problem of non-homogeneous samples. FIG. 3, for example, shows an optical component 16 that is angled with respect to the laser beam striking it. As the optical component rotates by discrete amounts, the laser beam is directed to different locations on the sample. Therefore, a preferred method used locates the laser beam at a particular spot on the sample, finds the correct focal length by translating the focusing lens 14, and then performs the cleaning operations as described above, followed by the sample analysis. The optical component 16 is then rotated a discrete amount, for example 60 degrees, to yield a different sample location which it is also cleaned and analyzed. At each location, the optimal focus is determined and saved for the laser spot on the sample as described above. In a further embodiment, if the analytical results (e.g., the concentration of the top five elements changes by 10% or less) for a second or third testing location are not appreciably different than the first testing location, the controller terminates the measurement process and the controller averages the results. Thus, for homogeneous samples, only two to three locations are cleaned and analyzed conserving power in a battery operated device. For non-homogeneous sample, five locations may be cleaned and analyzed. The controller is preferably configured to report to the operator when the sample is homogeneous and/or non-homogeneous. Note that XRF techniques are not able to determine if a sample is non-homogeneous.

Figure 8:
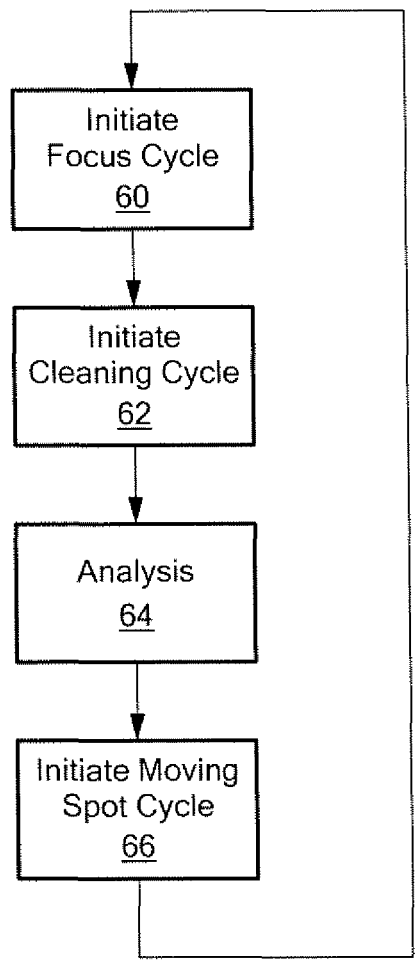
FIG. 8 is a flow chart depicting the primary steps associated with a method in accordance with the invention and/or the programming and/or configuration of the controller depicted in FIGS. 1-3.

FIG. 8 depicts the processing of controller 12, FIGS. 1-3 in one preferred embodiment. The focusing cycle is initiated, step 60, in response to a trigger signal followed by the cleaning cycle, step 62, for each sample location. These cycles may be reversed. At each location on the sample, the spectrum analysis is performed, step 64, wherein the elemental concentrations are computed, reported, and typically saved. The hand held portable unit, see FIG. 12, preferably has a display screen for displaying the elements present in the sample, their concentrations, and other data. In general, the controller subsystem is configured, (e.g., programmed) to pulse the laser producing a series of laser pulses and to process the resulting signals from the detector (spectrometer) subsystem to determine one or more elemental concentrations in the sample. For LIBS analysis, the detector outputs signals representing intensities at different wavelengths defining the elements in the sample and the various concentrations.

The laser beam spot is then moved, step 66 whereupon the focusing, cleaning, and analysis cycles repeat for the new sample location. Sequential locations are thus analyzed.

In the focusing cycle, the controller is configured to adjust the focusing lens, step 70, pulse the laser, step 72, and analyze the intensity data reported by the detector electronics, step 74 (see FIGS. 4A-4C) until an optimum intensity is detected (which is at or near the maximum), step 76. The lens position which resulted in the optimum intensity is stored, step 78. A memory accessed by the controller may be used to store lens position values, calibration constants, spectral data, algorithms, computer code, and the like. FIG. 5 demonstrate an optimum focus location in the range of positions 4 to 7.

Figure 10:
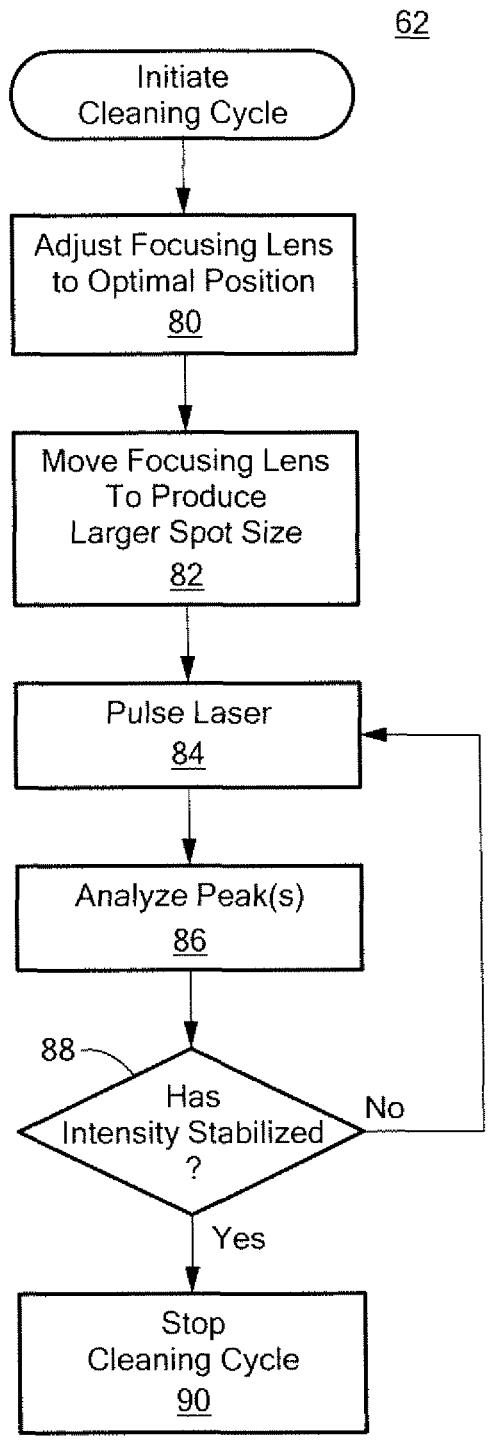
FIG. 10 is a flow chart depicting the primary steps associated with the cleaning cycle of FIG. 8.

In the cleaning cycle, FIG. 10, the focusing lens is moved to the optimal position, step 80, or optionally moved to produce a slightly larger spot size, step 82. The laser is repeatedly pulsed, step 84, and for each resulting plasma, one or more peaks are analyzed, step 86. The cleaning cycle stops when the intensity data indicates the intensity has stabilized, step 88 and 90 as shown in the example of FIGS. 6A and 6B.

Figure 11:
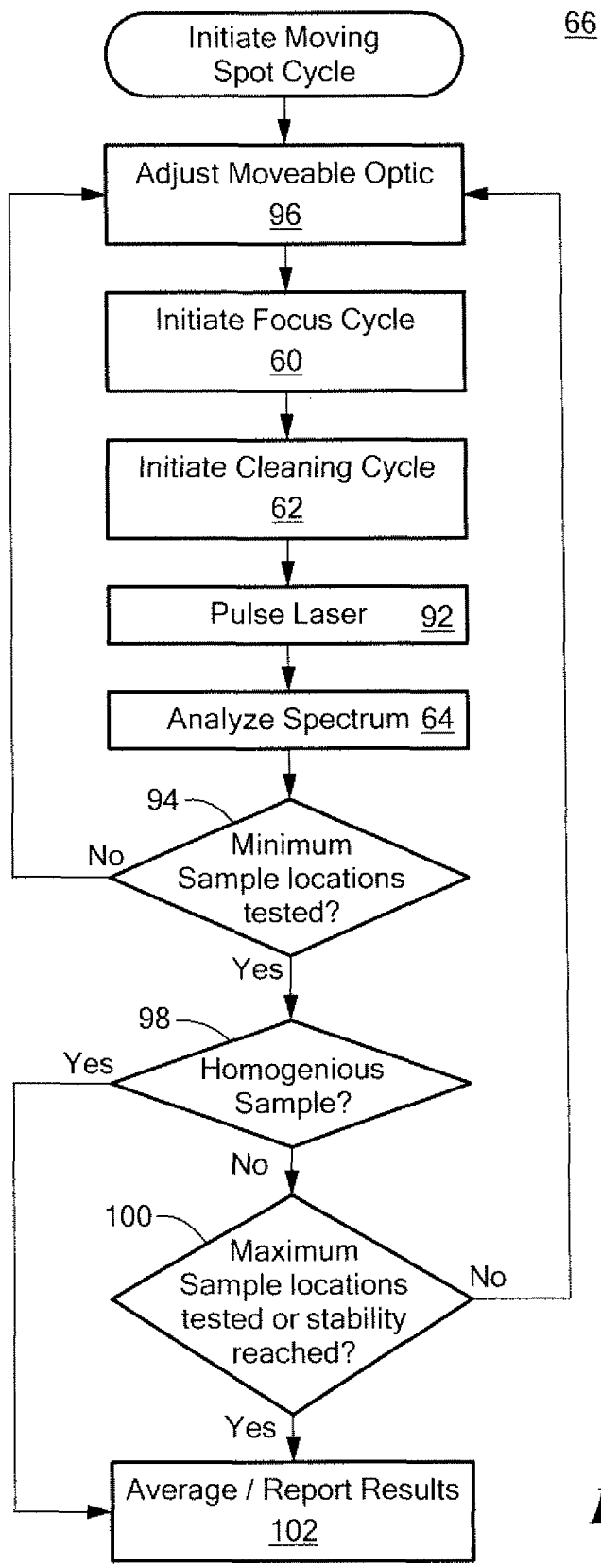
FIG. 11 is a flow chart depicting the primary steps associated with the moving spot cycle shown in FIG. 8.

The moving spot cycle, FIG. 11, preferably includes running the focusing cycle, step 60 and running the cleaning cycle 62 at each location on the sample. At the optimal laser spot size, the laser is pulsed, step 92 and the spectrum is analyzed, step 64. Typically, a minimum number of sample locations are tested (e.g., 3), step 60 as depicted at 94 and if the minimum number has not been reached, the movable optic (14, FIGS. 1, 16, FIGS. 2-3) is adjusted to move the beam to a different location on the sample, step 96, FIG. 11. The focusing, cleaning, and analysis cycles are again repeated for this new sample location until the analysis as between different sample locations indicates a homogeneous sample as shown at 98 or a maximum number of sample locations (e.g., 5) have been tested, step 100 (for non-homogeneous samples). Alternatively, once the sample is determined to be non-homogeneous, a predetermined number of new sample locations may be analyzed. Preferably, the results are averaged for both homogeneous and non-homogeneous samples and reported, step 102.

The number of required sequential sampling locations may depend on how heterogeneous the sample is. It is desirable to minimize the required sampling time, so various algorithms may be employed as data is collected to optimize the sampling time required. One algorithm starts with a minimum sampling location count (3 locations for example) to establish a baseline variance or standard deviation in constituent concentration. If the standard deviation is above a pre-set threshold, then the algorithm will initiate further measurements from additional sample N locations.

Each time a new location is sampled, the standard deviation of the data set is calculated. The precision of the mean (or average) concentration is related to the standard deviation and the number of samples N in the data set by:

$$\sigma_{mean} = \frac{\sigma}{\sqrt{N}}. \tag{1}$$

The "standard deviation of the mean" is a measure of how stable the computed average of the measured concentrations are. The algorithm terminates further sample location measurements once the standard deviation of the mean is below a pre-set threshold. Often with such algorithms, a maximum sample location count is programmed to force the instrument to stop measuring after a certain time limit is reached. Such algorithms can also make estimates of time to completion based on the rate of improvement of the "standard deviation of the mean" (or similarly computed indicator) after the first several measurements. The user may be given the option to wait for completion or to stop the measurement.

Figure 12:
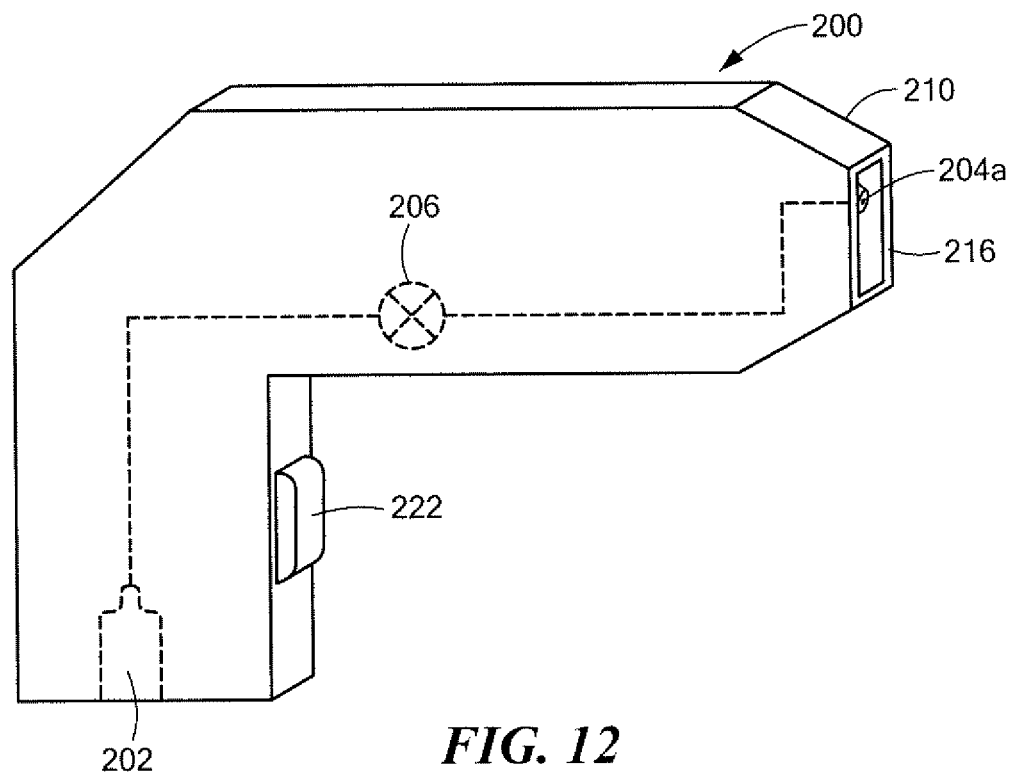
FIG. 12 is a schematic three dimensional view of a hand held battery powered LIBS spectrometer device in accordance with an example of the invention featuring a gas purge subsystem.

FIG. 12 shows a handheld portable unit housing the subsystems and components of FIGS. 1, 2, and/or 3 and with the associated electronic circuitry carrying out the analysis, signal processing, and control steps depicted above with respect to FIGS. 4-6 and FIGS. 8-11.

An argon purge subsystem may be included for better analysis of the sample for certain elements including sulfur, phosphorous, and/or carbon.

In some embodiments, the focusing lens adjustment cycle is performed without moving the laser spot to multiple locations on the sample and vice versa. The cleaning cycle is, in some embodiments, preferred and in another aspect is optional and/or separately patentable.

In one preferred embodiment, the hand held LIBS spectrometer is battery powered and employs an eye safe laser. The automatic focusing steps ensure repeatable, more accurate elemental concentration results without operator intervention. Automatic focusing provides more repeatable results, without operator intervention, and more accurate results.

The cleaning cycle ensures that the laser adequately cleans the sample while at the same time saves testing time and battery power because, once the sample is adequately cleaned, no more cleaning laser pulses are needed. This reduces the number of laser shots and therefore makes the test conclude faster and saves battery power.

Adequate sampling of all samples is performed and battery power and testing time are conserved.

Figure 13:
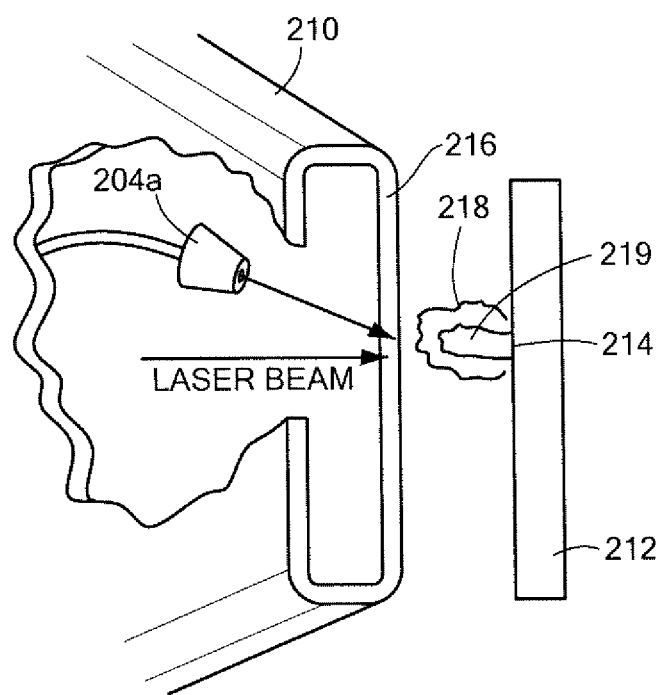
FIG. 13 is a schematic view showing a portion of the device of FIG. 12.

FIG. 12 shows one example of a battery powered, portable LIBS analyzer 200 with gas (e.g., argon) cartridge 202 loadable therein. As shown in FIG. 13, one or more nozzles 204a is fluidly connected to cartridge 202 via valve 206, FIG. 12. In other examples, a cartridge or small tank is connected to unit 200 and carried in a small pack for field analysis.

Preferably, only a small supply of argon is required in the purge subsystem because the nozzle(s) is configured to deliver a small spray of argon gas locally in a small purge volume. Unit 200 may have a converging front nose 210 where the laser beam exits to strike sample 212 at location 214 (e.g., 5-100 μm in diameter) creating a plasma 219. Nozzle 204a is just inside distal nose 210 proximate end wall 216 and oriented to produce an argon spray at (and preferably only at) location 214. The nozzle has an orifice configured to produce a purge volume of argon gas less than 1.0 cm$^3$, typically as small as 0.5 cm$^3$ as show at 218 so it just surrounds the plasma 219 and little argon is wasted. In one example, the argon gas volume was 0.125 cm$^3$. As discussed below, the flow rate is low and the argon purge is used only when needed in order to further save argon resulting in a LIBS analysis unit which does not require a large supply of inert gas.

Figure 14:
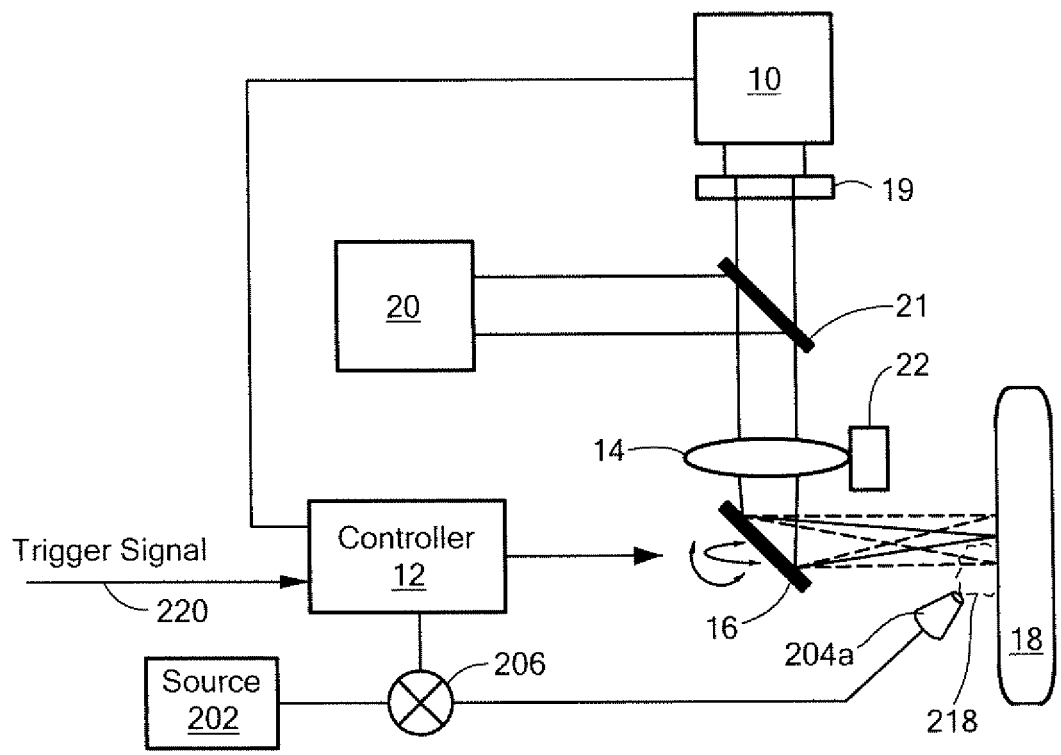
FIG. 14 is a block diagram showing the primary components associated with an example of a gas purge subsystem.

FIG. 14 shows controller 12 controlling solenoid valve 201 between source 202 and nozzle 204a. A trigger signal as shown at 220 (generated, for example, by pressing on trigger mechanism 222, FIG. 12) is received at controller 12 and, in response, controller 12 may optionally initiate the cleaning cycle as discussed above. Another trigger mechanism may include a physical or virtual button.

Figure 15:
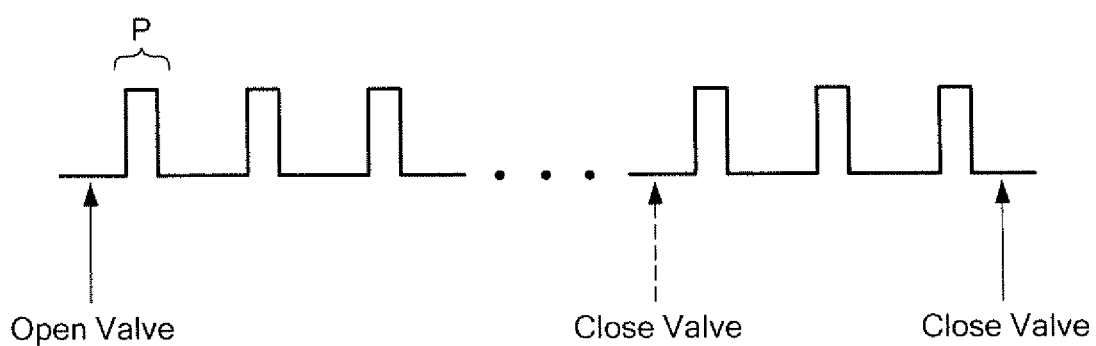
FIG. 15 is a timing diagram showing a number of laser pulses.
Figure 16:
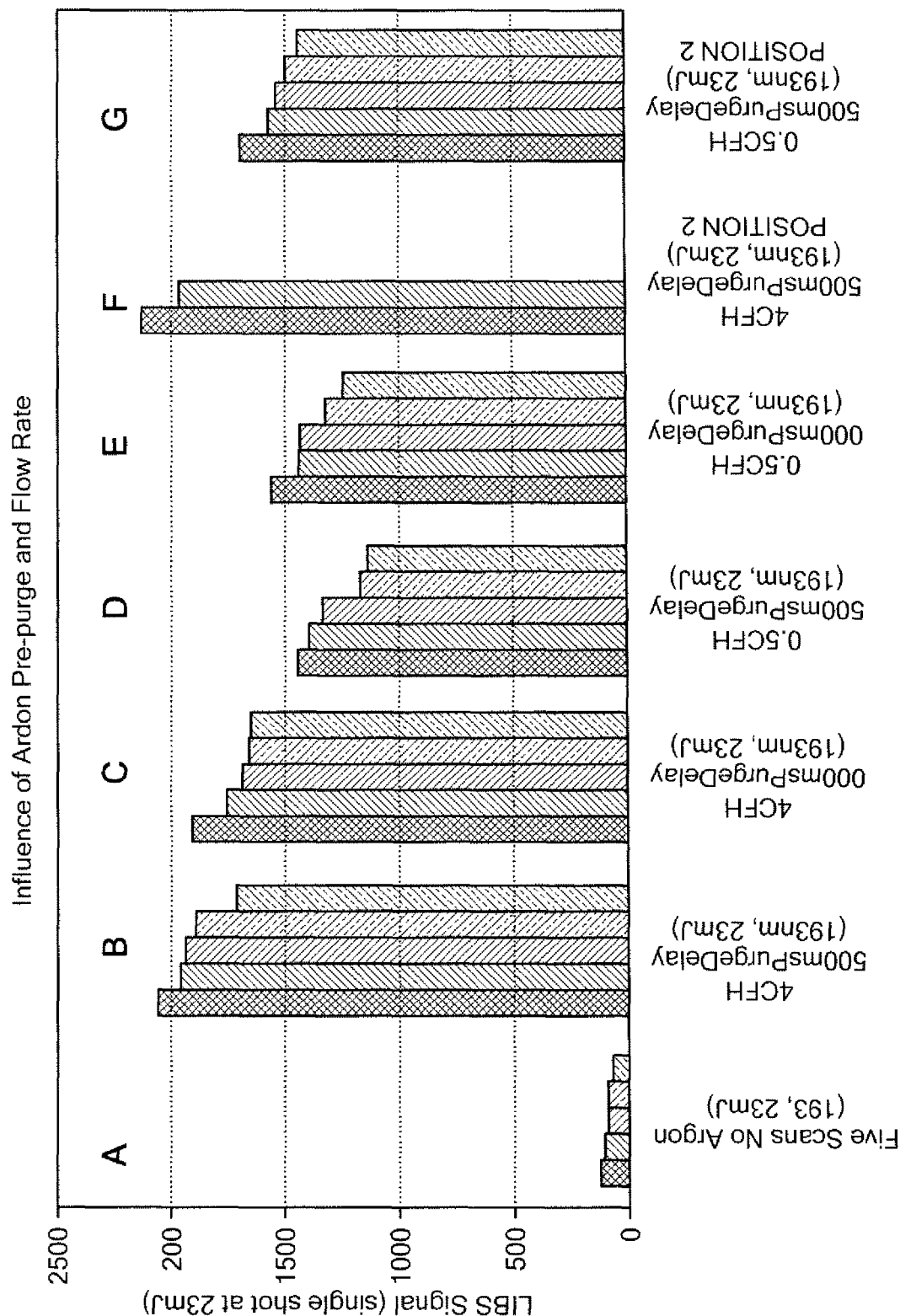
FIG. 16 is a graph showing the spectrometer signal strength for a number of purge conditions.

During the subsequent analysis cycle, controller 12 opens valve 206 just prior (e.g., 0.1-0.5 seconds before) the first plasma producing laser pulse as shown in FIG. 15. FIG. 16 shows a strong signal for carbon in a test sample even when the purge occurred just 0.1 seconds prior to the first laser pulse. Controller 12, FIG. 14 is further configured to close valve 206 shortly after the last laser pulse or even prior to the last laser pulse as shown in FIG. 15 in order to conserve the purging gas.

FIG. 16 depicts the influence of the flow rate, nozzle position, and purge timing on the resulting LIBS signal output by spectrometer 20, FIG. 14. In test A, no purge was used and the carbon peak was difficult to correctly decipher. In test B, the purge rate was 4 CFH, the nozzle was 0.2 cm away from the sample and the plasma location, and the purge gas was initiated 0.5 seconds before the first laser pulse. In test C, the nozzle position and the flow rate were the same as in test B but now the purge gas was initiated only 0.1 second before the first laser pulse. The signal strength was still very high. In test D, a lower flow rate of 0.5 CFH was used and the purge occurred 0.5 seconds before the first laser pulse while in test E the lower gas flow rate of 0.5 CFH was used and the solenoid valve was opened for a purge 0.1 seconds before the first laser pulse. In both cases, the signal strength was sufficiently high. In test F and G the nozzle was brought closer to the sample (0.1 cm away from the sample). In test F a flow rate of 4 CFH was used with a 0.5 second purge delay and in test G a 0.5 CFH flow rate was used with a 0.5 second purge delay.

Accordingly, it is possible to use a very low flow rate of 0.5 CFH and a very short (0.1 second) delay before the first laser pulse and still obtain a sufficiently strong signal from the resulting photons. A purge rate of less than 2 CFH may be optimal.

In one typical scenario, the output of spectrometer 20 is analyzed between the laser pulses shown in FIG. 15. In some examples, if the valve can be actuated at a high frequency rate, the gas can even be turned off between laser pulses and then on again just prior to each laser pulse.

Thus, in one preferred embodiment, an improved signal is generated and detected by the spectrometer using an inert gas purge. The gas is conserved by using a low flow rate and a smaller size nozzle properly located and oriented to produce a small volume purge spray. And, the purge is used only when required. One result is the ability to use only a small cartridge as opposed to an unwieldy tank in a portable, hand held, battery powered system. When one cartridge is emptied, another full cartridge can be quickly loaded into the unit.

Figure 17:
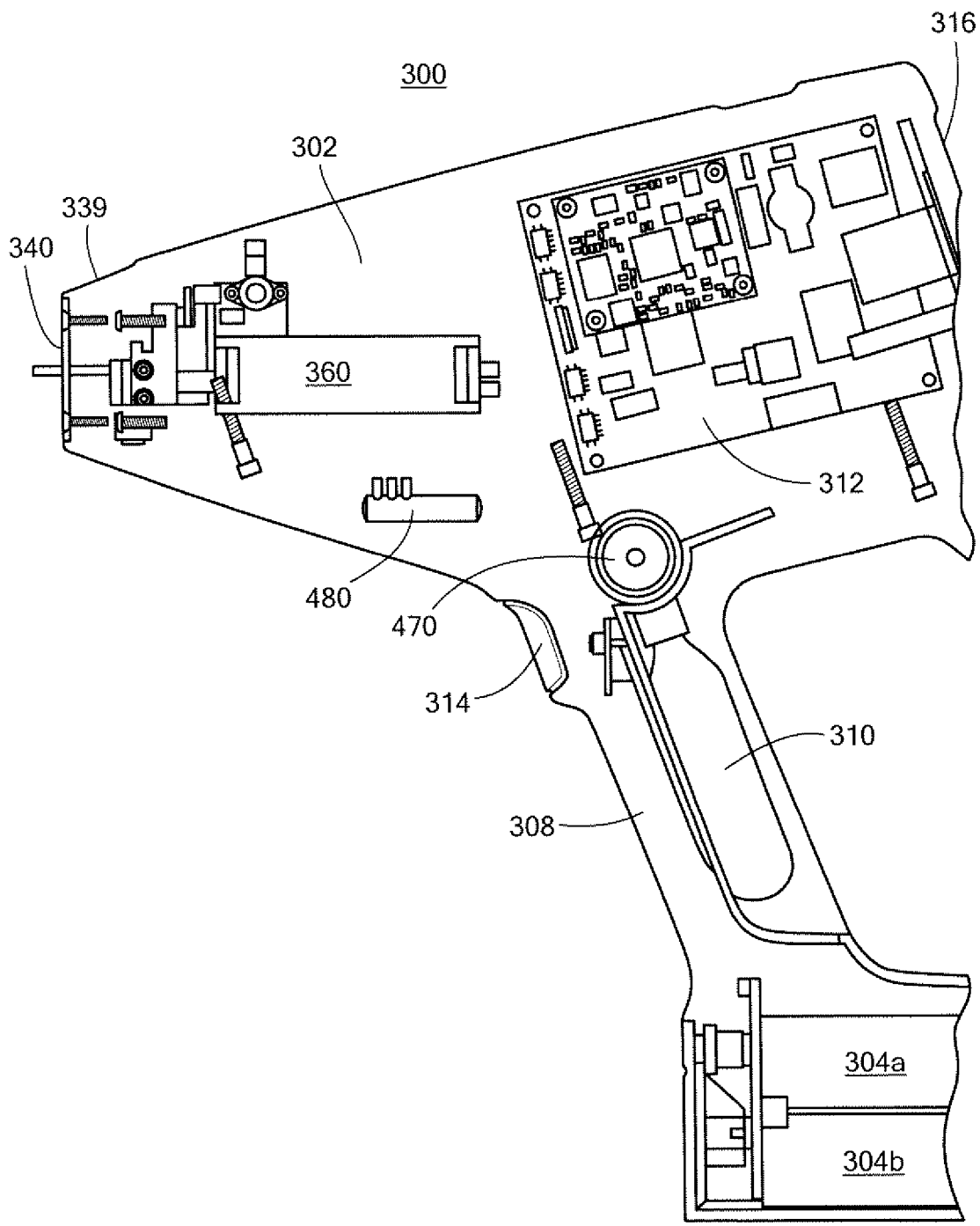
FIG. 17 is a schematic side view of an example of a handheld LIBS spectrometer system in accordance with the invention.

In one embodiment, handheld LIBS spectrometer 300, FIG. 17 includes an eye safe laser (e.g., Kigre MK88) and functions to automatically focus the laser beam, move the laser beam focus, clean the sample using the moving laser beam, and auto-calibrate.

Shown in this particular example is housing 302 roughly in the shape of a pistol like device with rechargeable batteries 304a and 304b providing power to the subsystems of the device. The top portion of the housing may be made out of aluminum for laser heat dissipation and bottom half may be plastic. Handle or grip portion 308 includes a replaceable gas (e.g., argon) cartridge 310 therein. Printed circuit board 312 may include the necessary processing, signal conditioning, power supply, motor control, and other circuitry as described herein. Addition circuit boards may be included. Printed circuit board 312 may include one or more field programmable gate arrays programmed as set forth herein.

Trigger 314 is used to actuate a laser inside laser enclosure 360 fixed to housing 302. LCD display 316 may be included at the rear or top of the housing to display the results of an analysis, to enter commands, and the like.

FIG. 18 shows optics stage 320 including optics head 322 mounted in the forward section of the housing and including laser focusing lens 324 mounted in laser beam channel 326 and detection lens 328 mounted in detection channel 330. Camera 332 and camera lens 334 may also me mounted in optics head 322. The optics stage is configured to move the optics head relative to the housing. The laser source provides a laser beam depicted at 336 focused by lens 324 and directed to and exiting an aperture 338 in nose section 339 end plate 340 defining a minimum volume purge chamber 341 with optically transparent shield 342 disposed between optics head 322 and purge chamber 341. The transparent optical shield in front of the laser focusing lens 324 and detection lens 328 may be made of fused silica, quartz, or sapphire for example and functions to protect laser focusing lens 324 and detection lens 328 of the optic stage, which are very close to the front end of the device, from plasma generated by the laser exiting end plate 340 orifice 338 abutting a sample to be analyzed. End plate 340 and/or shield 342 can be removed from the housing (by removing fasteners such as screws) and cleaned or replaced by the user as necessary when shield 342 becomes dirty, pitted, or the like. The optical shield also functions to create a small chamber for argon containment. It also serves to protect the optical elements from the outside environment.

Purge chamber 341 is preferably purged with an inert gas such as argon as discussed herein supplied by cartridge 310, FIG. 17.

The laser beam 336, FIG. 18 is focused to a small spot size by lens 324 onto a sample adjacent end plate 340. Typically, end plate 340 is placed on the sample to be analyzed. The resulting plasma and electromagnetic radiation emitted from the plasma passes through aperture 338 and is focused by detection lens 328 into detection channel 330. A wave guide such as a fiber optic bundle may be coupled to detection channel 330 at port 350 and couples the electromagnetic radiation to a spectrometer subsystem preferably including an array of individual spectrometer enclosures as discussed herein. The spectrometer subsystem provides an output to the controller subsystem which controls the firing of the laser source and commands one or more motors configured to advance and retract optics stage 332, to move it left and right, and/or to move it up and down. In this way, the laser beam can be automatically focused, can be used to clean the sample by moving the laser beam about the sample, can be used to take readings at different locations on the sample, and to auto-calibrate the system.

Beam translation on the sample surface makes use of the property of a focusing lens 324, FIG. 19 to focus all incoming parallel light rays to a single point collinear with the center of the lens. A collimated beam of light (parallel light rays) entering the lens is focused to a point. Collimated beams of smaller diameter are still focused to a point at the same location. Moving the beam relative to the lens while keeping it parallel to the lens optical axis does not change the location of the focus.

If, however, the beam is kept stationary and the lens 324 is moved relative to the beam, the focused spot will also move relative to the stationary collimated beam. When the focusing lens is translated normal to the collimated beam, the focused spot will move in exactly the same direction and degree normal to the collimated beam. The focused spot will always be on the optical axis of the focusing lens. Detection optics 328 directed at that same point on the focusing lens optical axis and which is moved along with the focusing lens will thus be able to exactly track the beam as it is moved around on a sample surface.

Figure 19A:
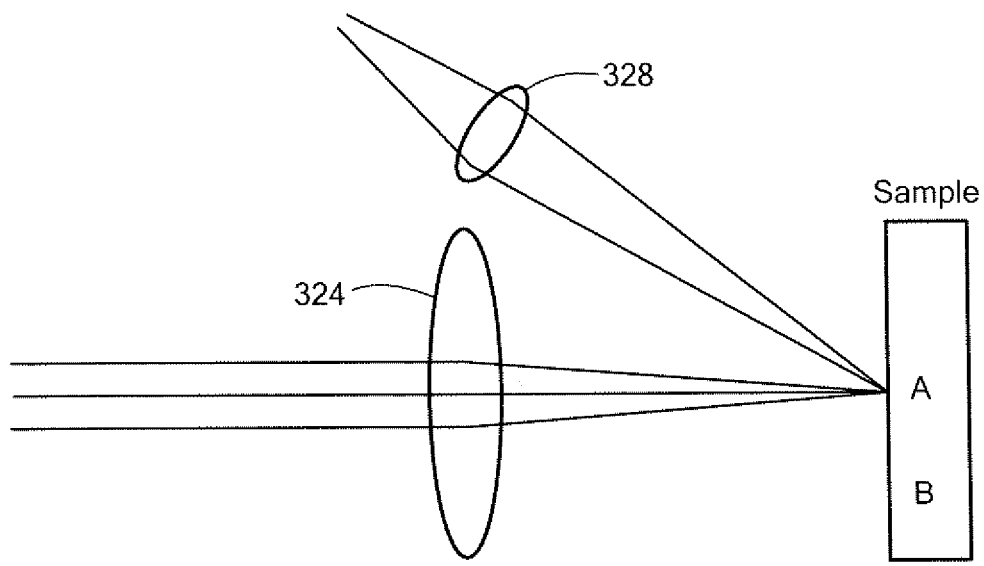
FIGS. 19A and 19B show how the laser beam is moved on a sample to generate a plasma at numerous locations detected by the detection lens of the optics head.
Figure 19B:
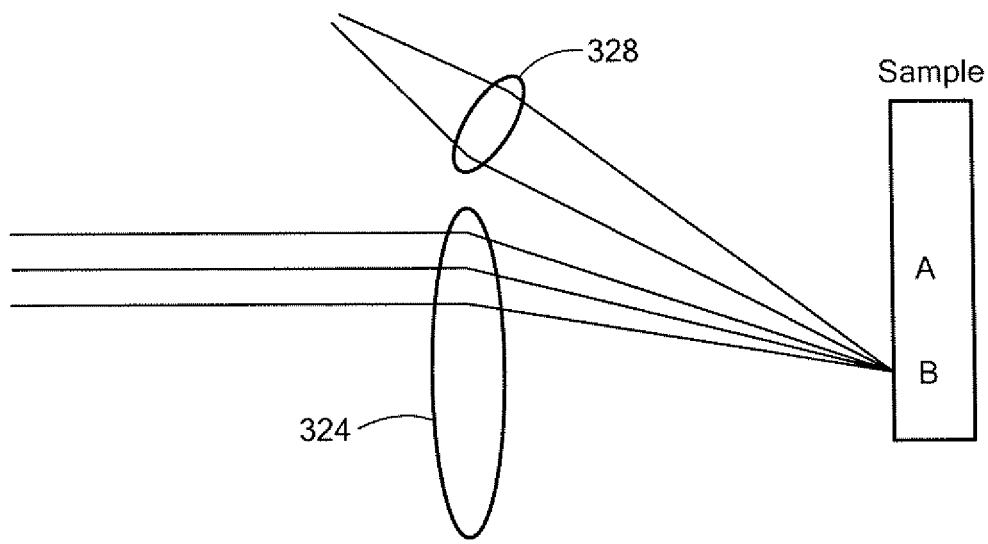

The detection optics 328 are directed at the same point to collect light for spectroscopic measurement and focus the electromagnetic radiation resulting from the plasma generated by the laser spot on the sample. FIGS. 19A and 19B show how both the focusing lens and collection optics are translated normal to the collimated beam (downward in the diagram) while the collimated beam and sample remain stationary. The focus and detection optics are both translated to move the laser spot from point A to point B on the sample.

A system of guide rails, bearings, rotary motors, and threaded drivers can be used to move the optics head 322 relative to the housing. In one particular example shown in FIGS. 20-22, the optics stage includes moveable optics 322 head in front of laser source 360 and first Z-shaped frame member 362 moveably coupled to the housing via plate 364, FIG. 20 and slideable right and left via linear bearing 366 attached to frame 362 and rail 368 attached to plate 364. There are means for moving the optics head. In one example, motor $m_1$ is attached to plate 364 with shaft $s_1$ driving nut $n_1$ engaging or formed in first frame 362 as shown at 340. This arrangement moves first frame 362 and the optics head 322 right and left relative to the housing and the nose section thereof.

Figure 20:
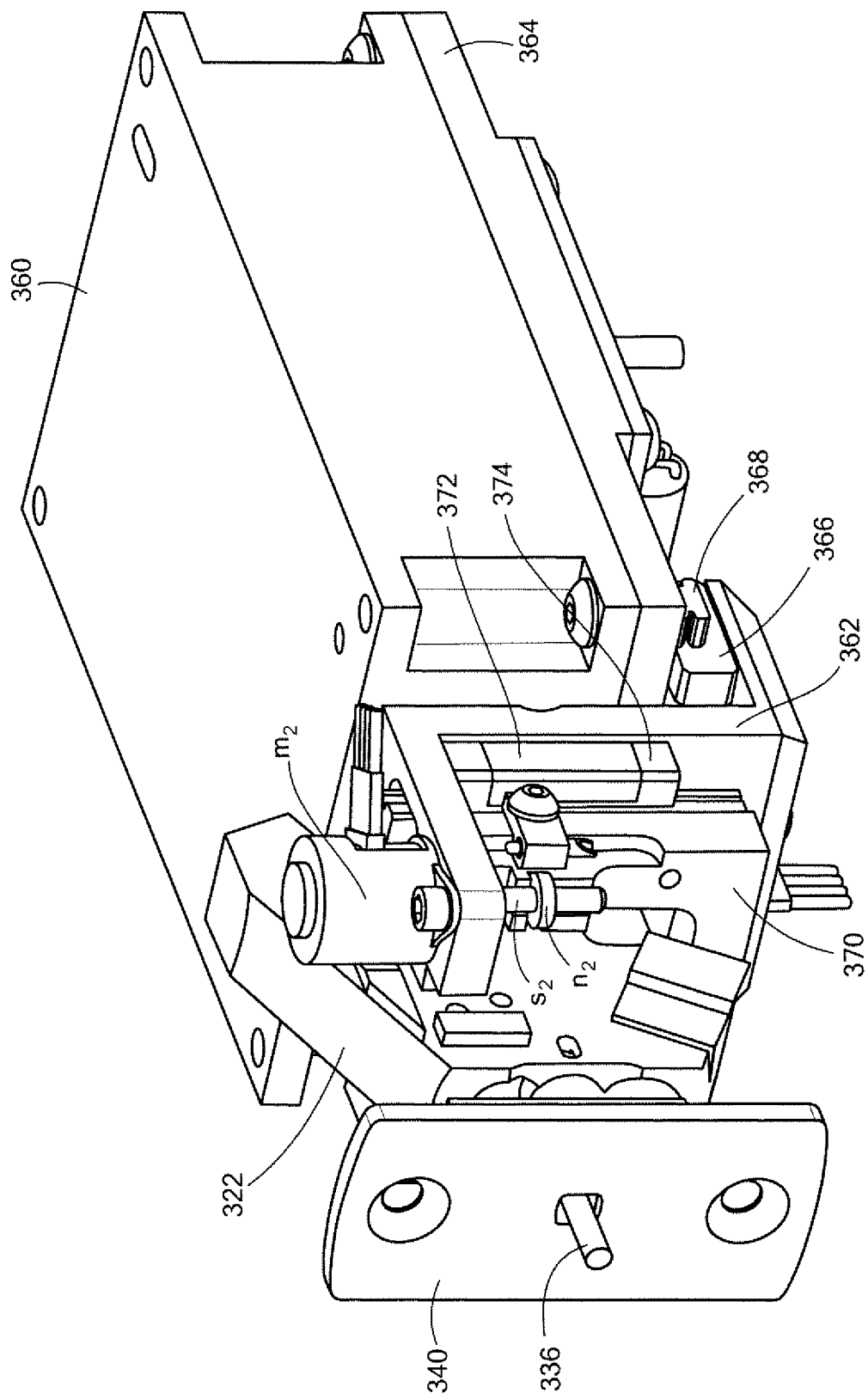
FIG. 20 is a schematic front view showing components of the optical stage for moving the optics head of FIG. 18.
Figure 21:
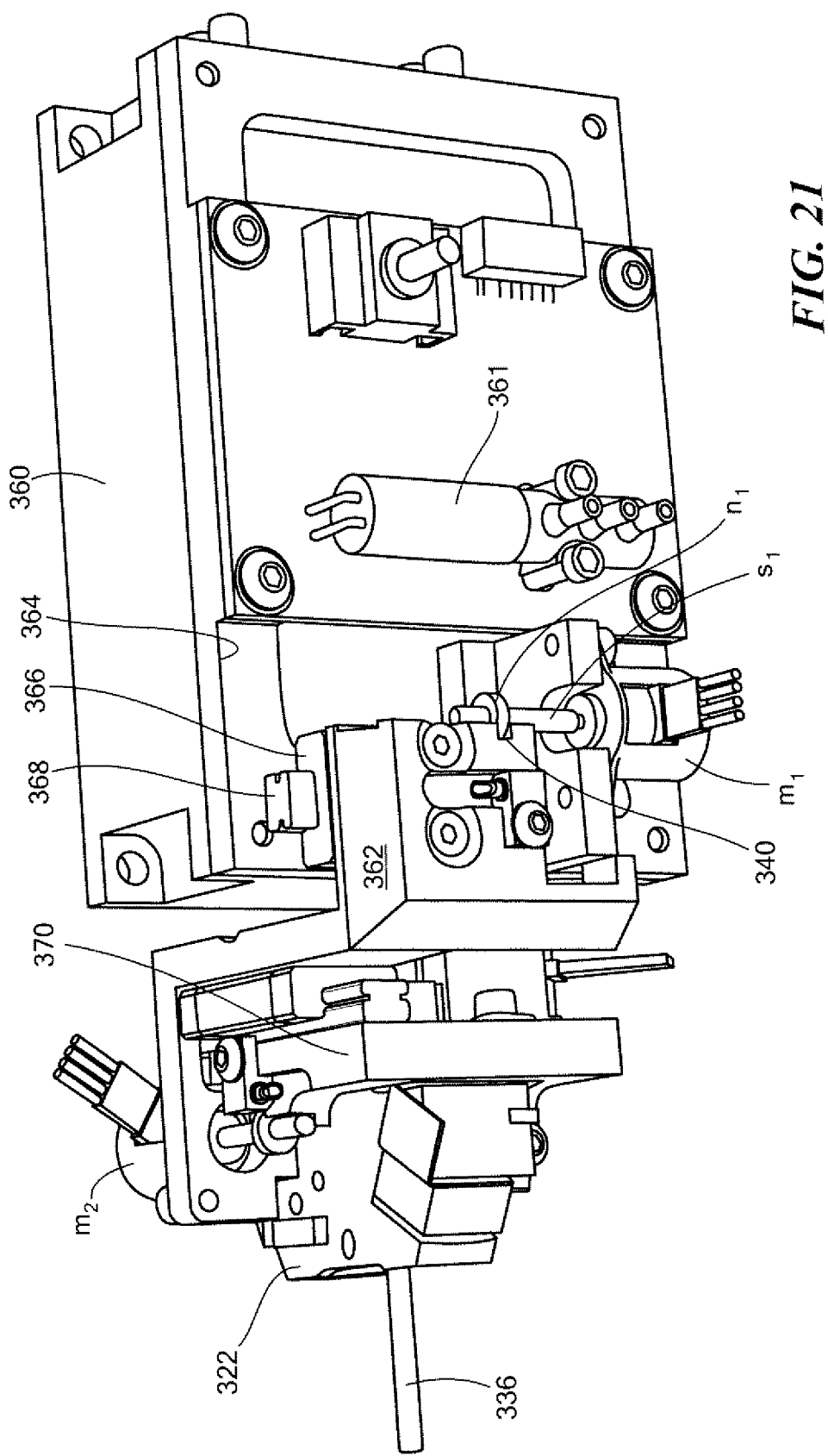
FIG. 21 is a schematic bottom view again showing components of the optics stage.

U-shaped frame member 370, FIG. 20 moves up and down relative to frame member 362 via linear bearing 372 attached to frame member 362 and a rail 374 attached to frame member 362. Motor $m_2$ is fixed to frame member 362 and shaft $s_2$ thereof drives nut $n_2$ engaging frame member 370. This arrangement moves frame member 370 and optics head 322 up and down relative to the housing and nose section.

Figure 22:
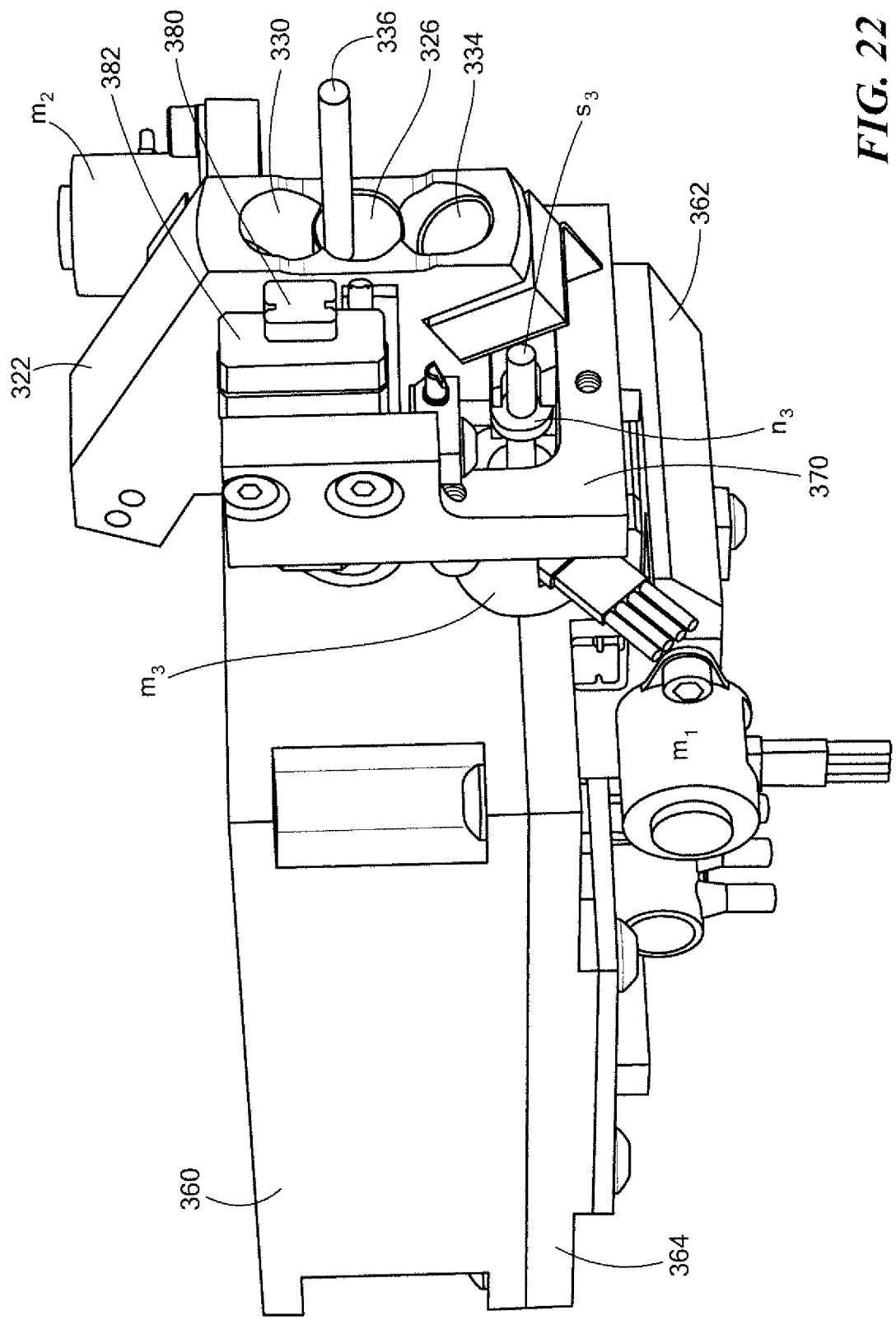
FIG. 22 is a schematic front view showing additional details concerning the optics stage.

As shown in FIG. 22, rail 380 is attached to optics head 322 and linear bearing 382 is attached to frame member 370. Motor $m_3$ is attached to frame member 370 and shaft $s_3$ thereof drives nut $n_3$ engaging optics head 322 for advancing and retracting the optics head in the direction of the laser beam from the laser source relative to the housing and nose section thereof.

Such movements under the control of the controller subsystem can be used to autofocus the laser beam. Movement of the optics head up and down and left and right can be used to automatically clean the target sample, move the focused laser beam about the sample for measurement at multiple sample positions, and calibrate the system. Other types of motors and bearing may be used including linear motors, piezo motors fluidly actuated motors, and the like. Other frame or stage members are possible. In other embodiments, the optics head has only one or two degrees of freedom.

In some embodiments, laser focusing lens 324 can be moved (e.g., translated) independently of detection lens 328 by incorporating a motor for laser focusing lens 324. A motor drive similar to that used in a cell phone camera zoom lens can be used. See U.S. Pat. No. 7,309,943 incorporated herein by this reference. The detection lens may be moved independently as well using a similar motor.

In one example, the end plate 340, FIG. 18 is made of or includes a portion 343 made of a calibration standard material e.g., 316 stainless steel. The presence of more than one material is also possible for more precise calibration over large wavelength ranges. The optics head is moved automatically to aim the laser beam at portion 343 and automatically focus it there to a small spot size. Electromagnetic radiation from the resulting plasma is received at optic lens 328 in detection channel 330 and processed by the spectrometer subsystem and controller subsystem for calibration purposes. Then, the optics head may be automatically moved to aim the laser beam at the sample through aperture 338, to focus the laser beam on the sample, to clean it, and then to test the sample at various locations. Preferably, autofocusing occurs at each sample location to account for surface irregularities, dimples, crevices, and the like.

Figure 23:
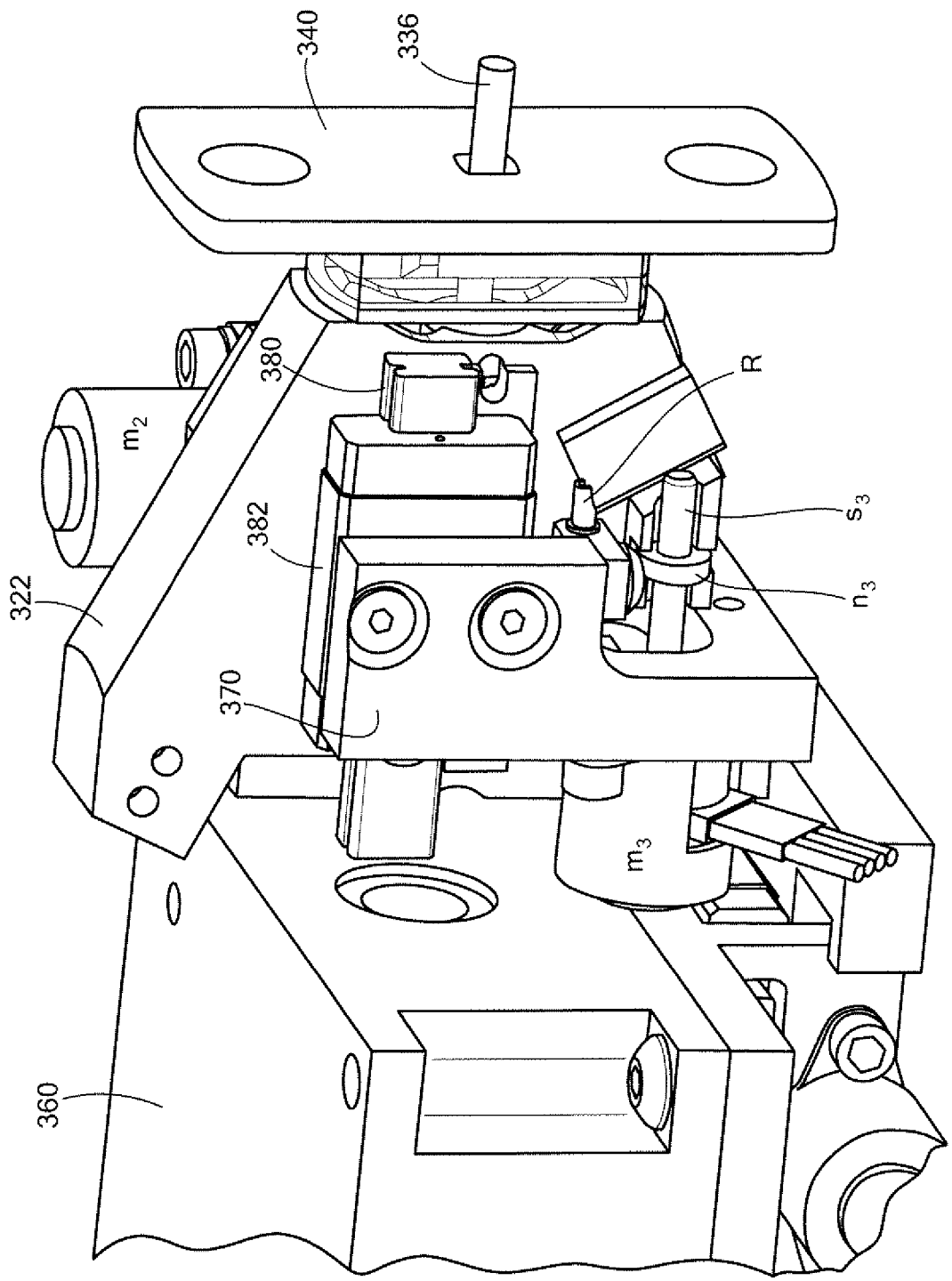
FIG. 23 is a schematic left hand side of the optics stage and optical head.
Figure 24:
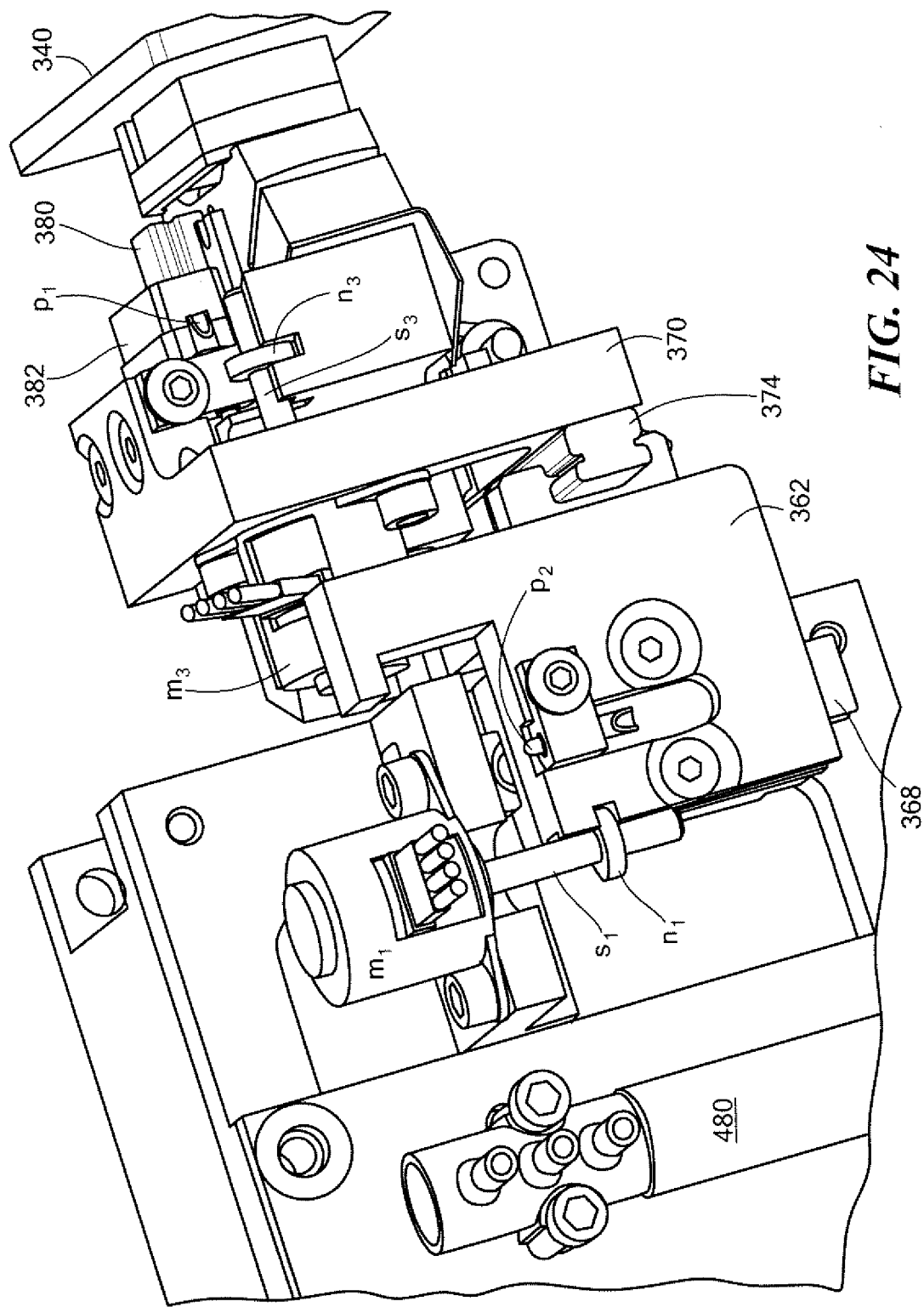
FIG. 24 is a schematic bottom view showing components of the optics stage and the optics head.

FIGS. 23-24 show different views of the frame members, motors, bearings, and the like. Also shown are sensors (e.g., pogo pins) $p_1$, $p_2$, configured to sense the end of travel of the two frame members and the optics head. For example, pin $p_2$ is used to detect the end of travel left position of frame member 362 while pogo pin $p_1$ is used to detect the end of travel rearward of the optic stage. Additional pogo pins, all providing an output to the controller subsystem, are used to detect end of travel right and left, up and down, and forward and rearward of the moving components so that controller subsystem and/or motor controllers can properly control motors $m_1$, $m_2$, and $m_3$ in a way which prevents any shock being applied to optics head 322.

Figure 25:
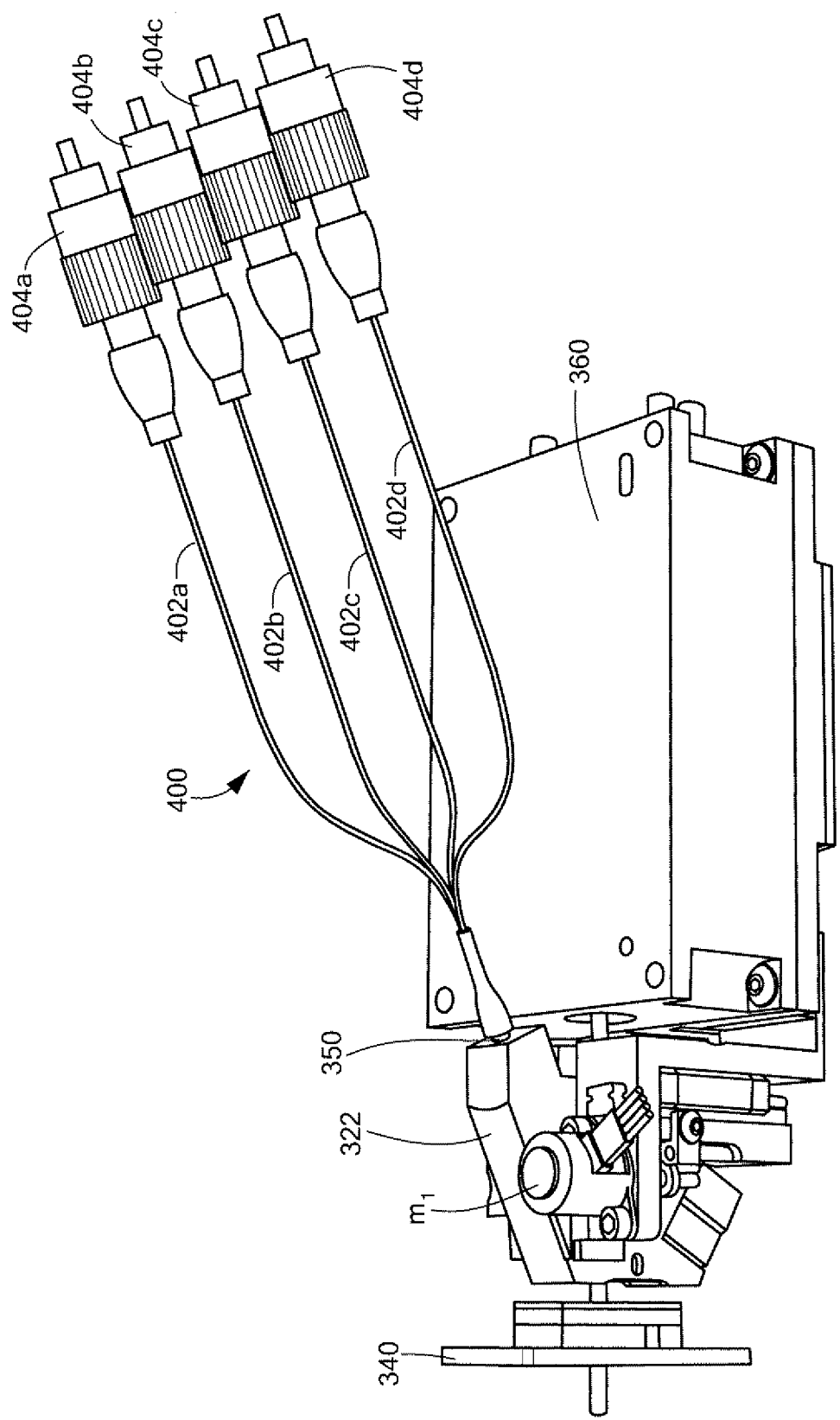
FIG. 25 is a schematic view showing the optics head coupled to fiber optic bundles.

FIG. 25 shows fiber optic bundle 400 coupled to optics head 322 detection channel port 350 with a plurality of optical channels such as fiber bundles 402a-402d terminating in couplers 404a-404d.

Figure 26:
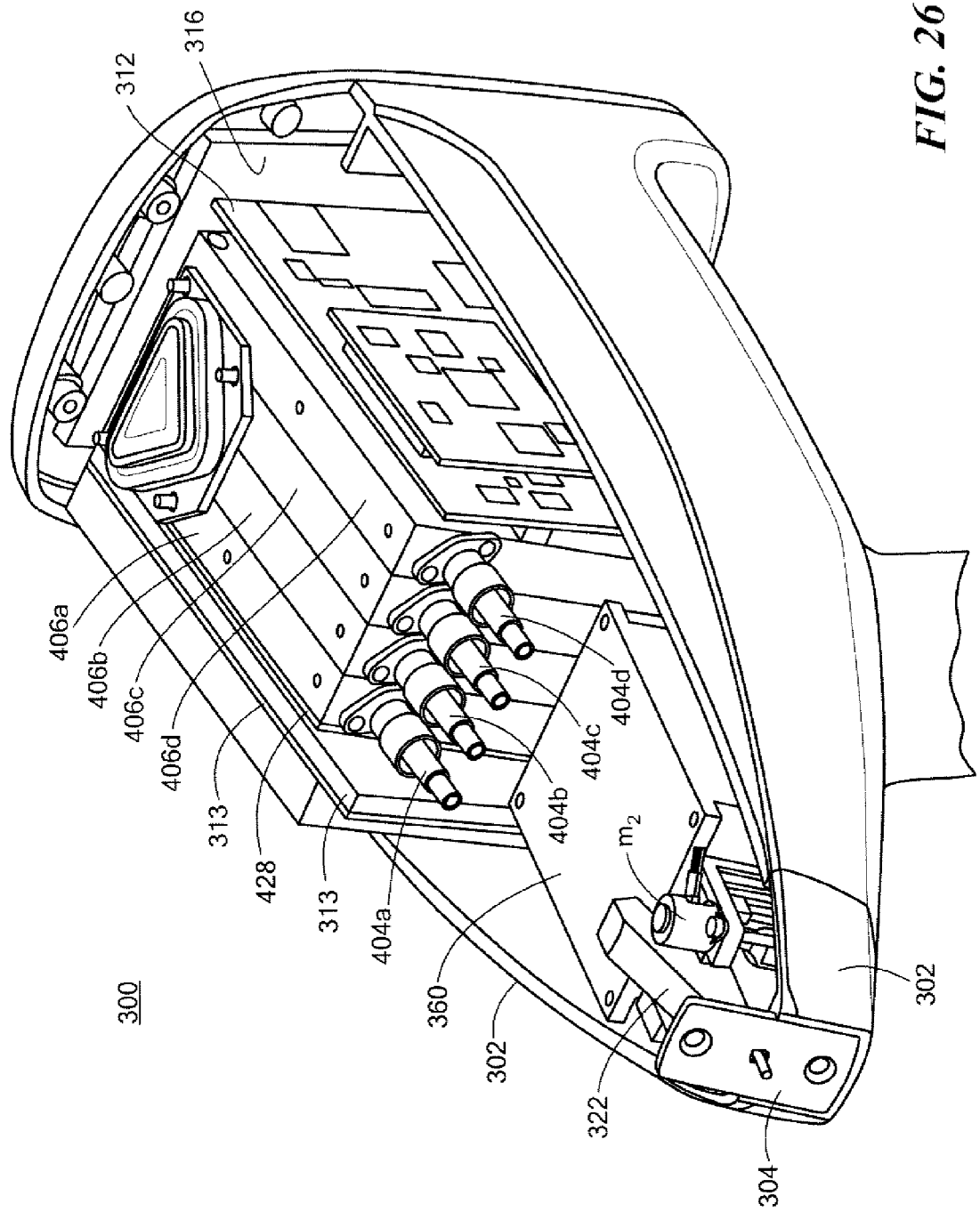
FIG. 26 is a schematic view showing the spectrometer subsystem enclosure array.

Each coupler is coupled to a spectrometer enclosure 406a-406d, FIG. 26 sandwiched between printed circuit boards 312 and 313 in housing 302 behind laser source enclosure 360 and in front of LCD display 316. All the spectrometer enclosures are preferably coupled together.

Figure 27:
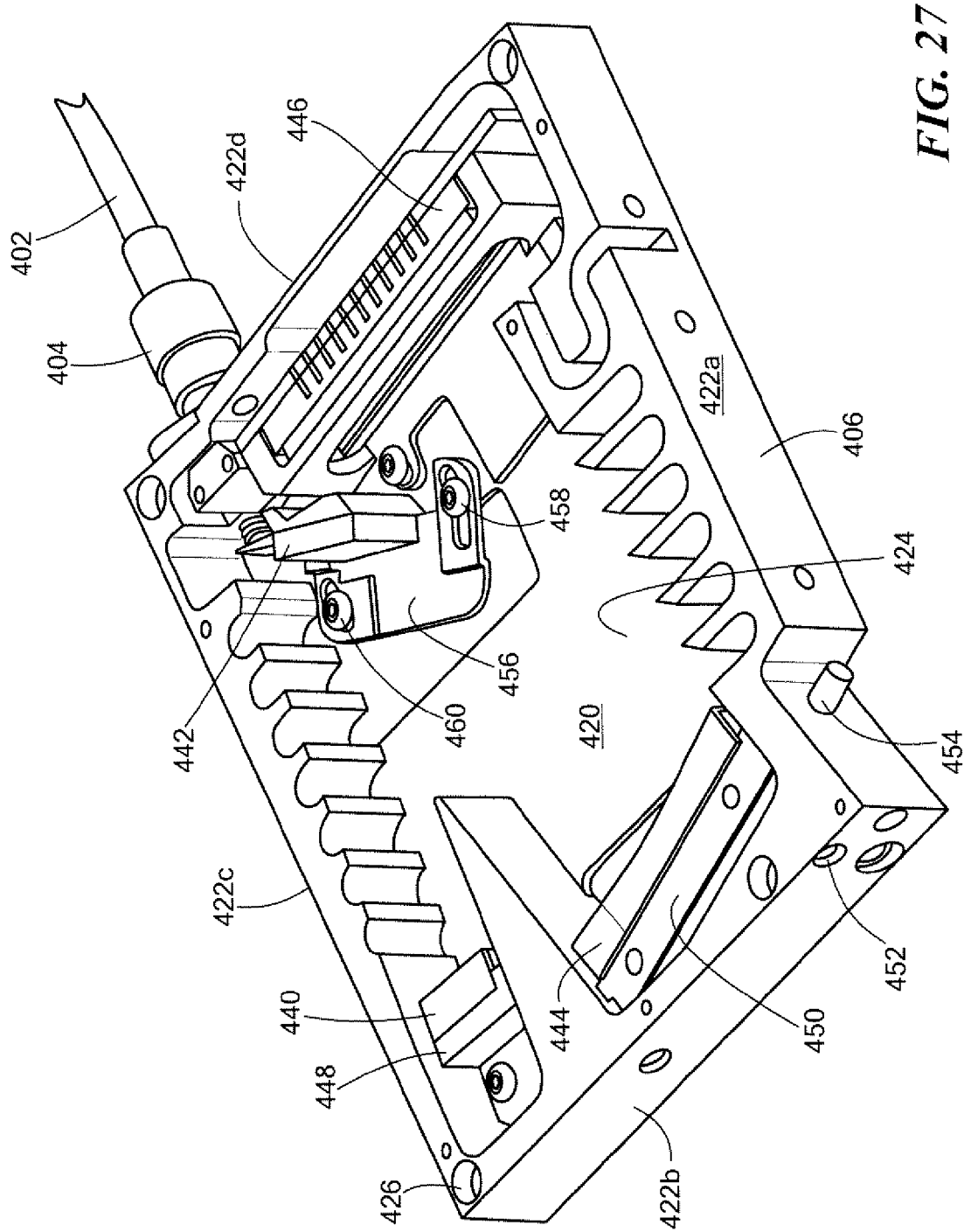
FIG. 27 is a schematic top view showing a spectrometer enclosure.

As shown in FIG. 27, each spectrometer enclosure 404 is thin (e.g., 0.5") and preferably about 4" long and 3" wide defining a floor 420 and four side walls 422a-422d and an open top with optical devices within cavity 424. The thickness of the enclosure is dictated by the tallest optical component therein.

In this way, to conserve space in a handheld device, the outside of the floor of one enclosure forms the top cover of an adjacent enclosure when the enclosures are coupled together via fasteners through enclosure corner holes such as shown at 426. The result is a more compact design. The structural configuration of each spectrometer enclosure is typically the same aside from differences such as grating, grating angle and input filter. This feature also reduces manufacturing costs. The final spectrometer enclosure in the array will typically include a lid 428, FIG. 26 covering its open top. The multiple spectrometers in an array provide a wide range of wavelengths and good resolution.

In one design, each spectrometer enclosure has optical devices in the design of a Czerny-Turner configuration. Here, electromagnetic radiation directed to an optical fiber 402 bundle from the detection channel of the optics head (resulting from the plasma generated by the laser beam) is redirected by mirror 440 which collimates the light and directs it to grating 442. The different wavelengths diffracted off of the grating are directed to mirror 444 which focuses the radiation on sensor 446 (e.g., a CCD sensor chip). The output of the CCD sensor is then provided to the controller subsystem for further processing, display, elemental analysis, and categorization by reference to spectrum reference libraries stored in memory, and the like.

Preferably, optical adjusters are provided where required, between the particular optic mount and the housing, to allow for precise alignment of the dispersed optical wavelengths to the CCD detector. For example, mirror 440 is mounted to fixture 448 coupled to but adjustable with respect to spectrometer enclosure floor 420. The angle of mirror fixture 450 can be adjusted via a set screw at 452 and mirror fixture 450 can be tilted via shaft 454. Grating fixture 456 can be adjusted via fasteners 458 and 460 received in spectrometer enclosure floor 420.

To tailor each spectrometer enclosure 406a-406d, FIG. 26 to a specific wavelength range, each enclosure may include different gratings and/or gratings disposed a different angles. The result is a handheld spectrometer which can detect a wide variety of elements. For LIBS applications, it is desirable to have a wavelength resolution of approximately 0.1 nm over a wavelength range from 175 nm to over 675 nm, a range of 500 nm or more. To cover 500 nm with 0.1 nm resolution, a minimum of 5000 pixels is required, ideally 50% more. Typical CCD pixel counts are 2048 to 3600. In this example, four spectrometers are employed utilizing 2048 pixels per spectrometer yielding just over 8000 total pixels.

Figure 28A:
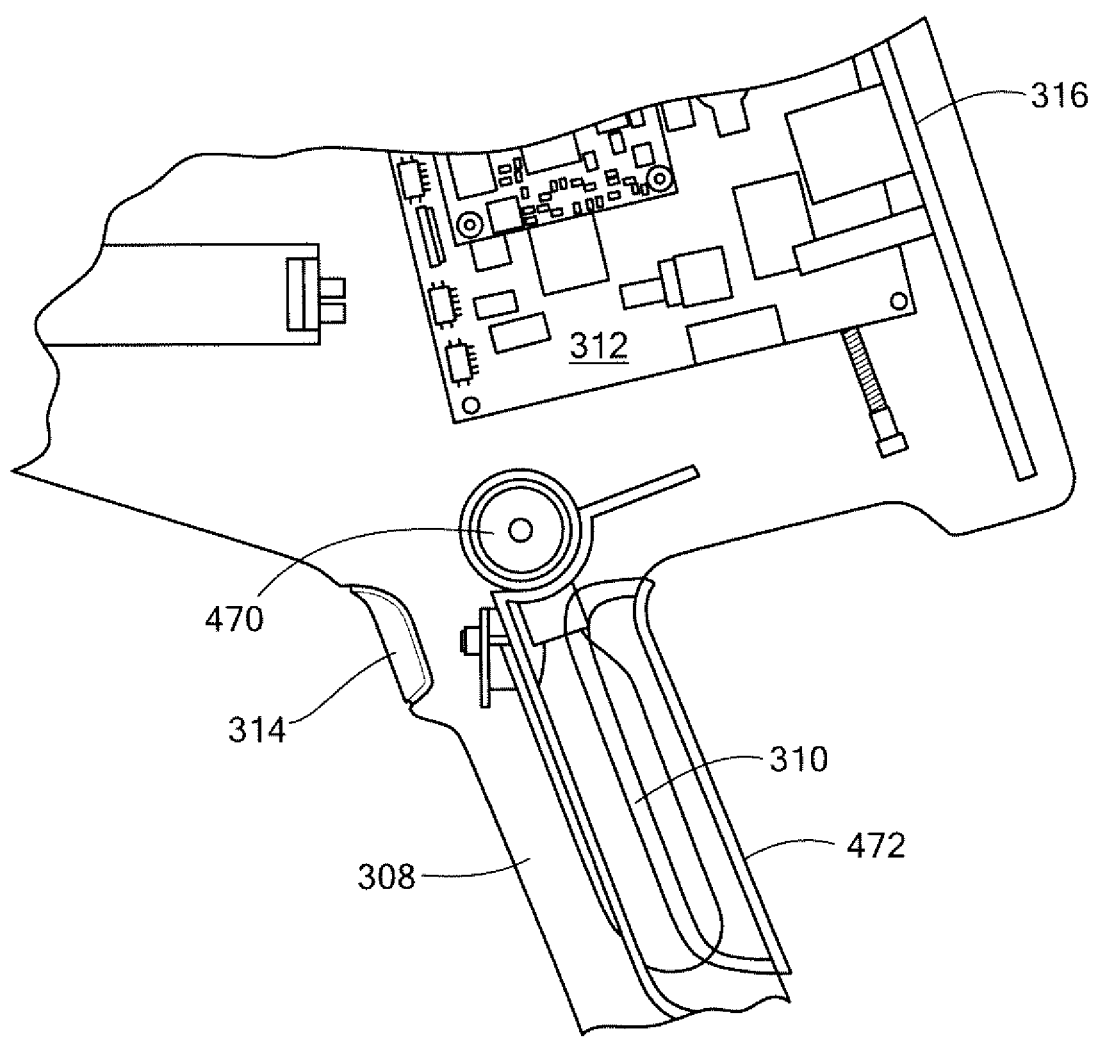
FIG. 28A is a schematic view showing a gas cartridge pivotably mounted in the handheld LIBS spectrometer handle portion.
Figure 28B:
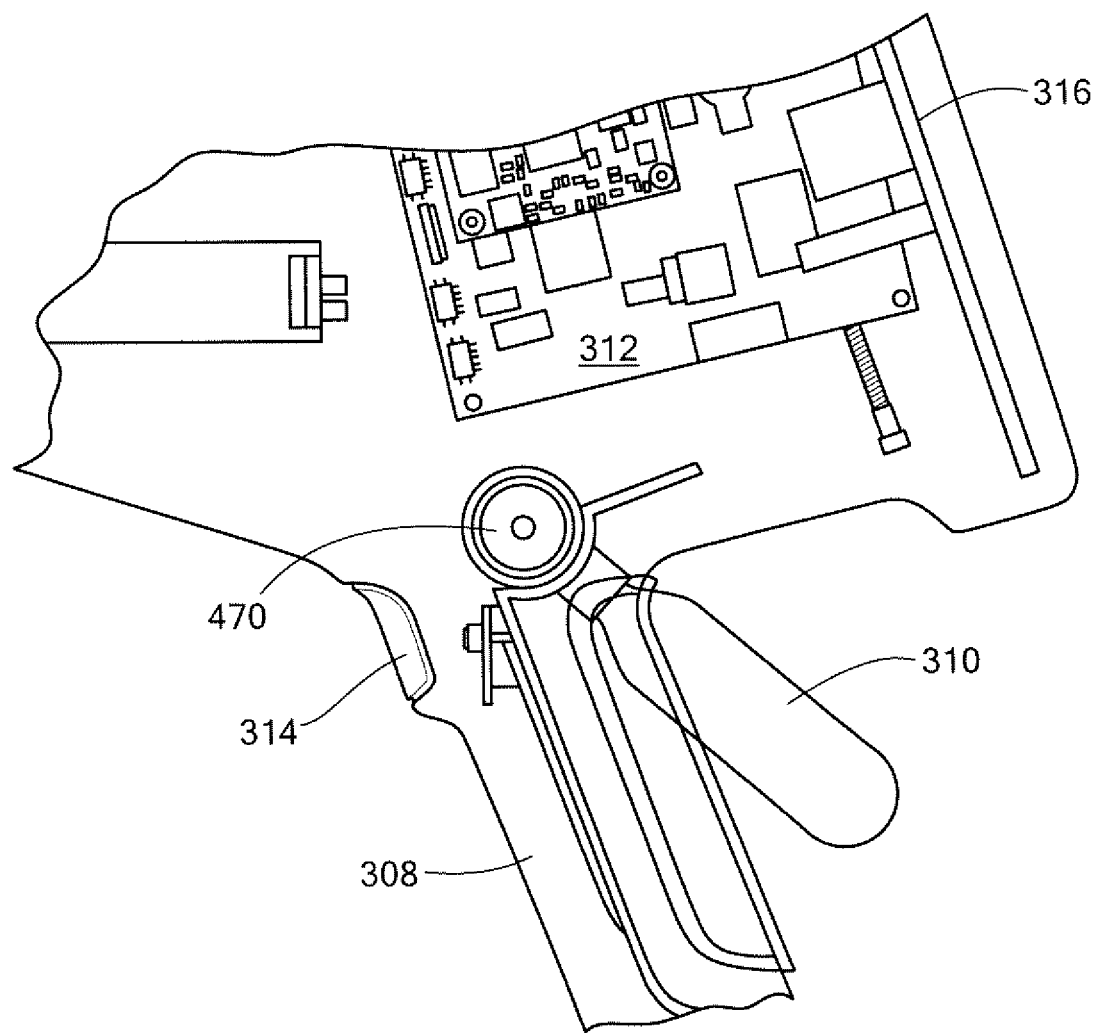
FIG. 28B is a schematic view showing the gas cartridge being pivoted out of the LIBS spectrometer handle portion for replacement.

As discussed above, gas cartridge 310, FIGS. 28A-28B is preferably disposed in handle section 308 behind door 472 removably coupled to regulator 470 itself rotationally coupled to the housing. In this way, the gas cartridge can be pivoted out of the handle for replacement. Regulator 470, in turn, is fluidly coupled to a valve such as solenoid 480, FIGS. 17 and 24 which is controlled by the controller subsystem. Solenoid 480, in turn is fluidly coupled to purge chamber 341, FIG. 18 between end plate 340 and shield 342. The only opening into purge chamber 341 is via aperture 338 in end plate 340 to conserve purging gas and preferably to eliminate the need to couple the handheld device to a large gas tank.

Figure 29:
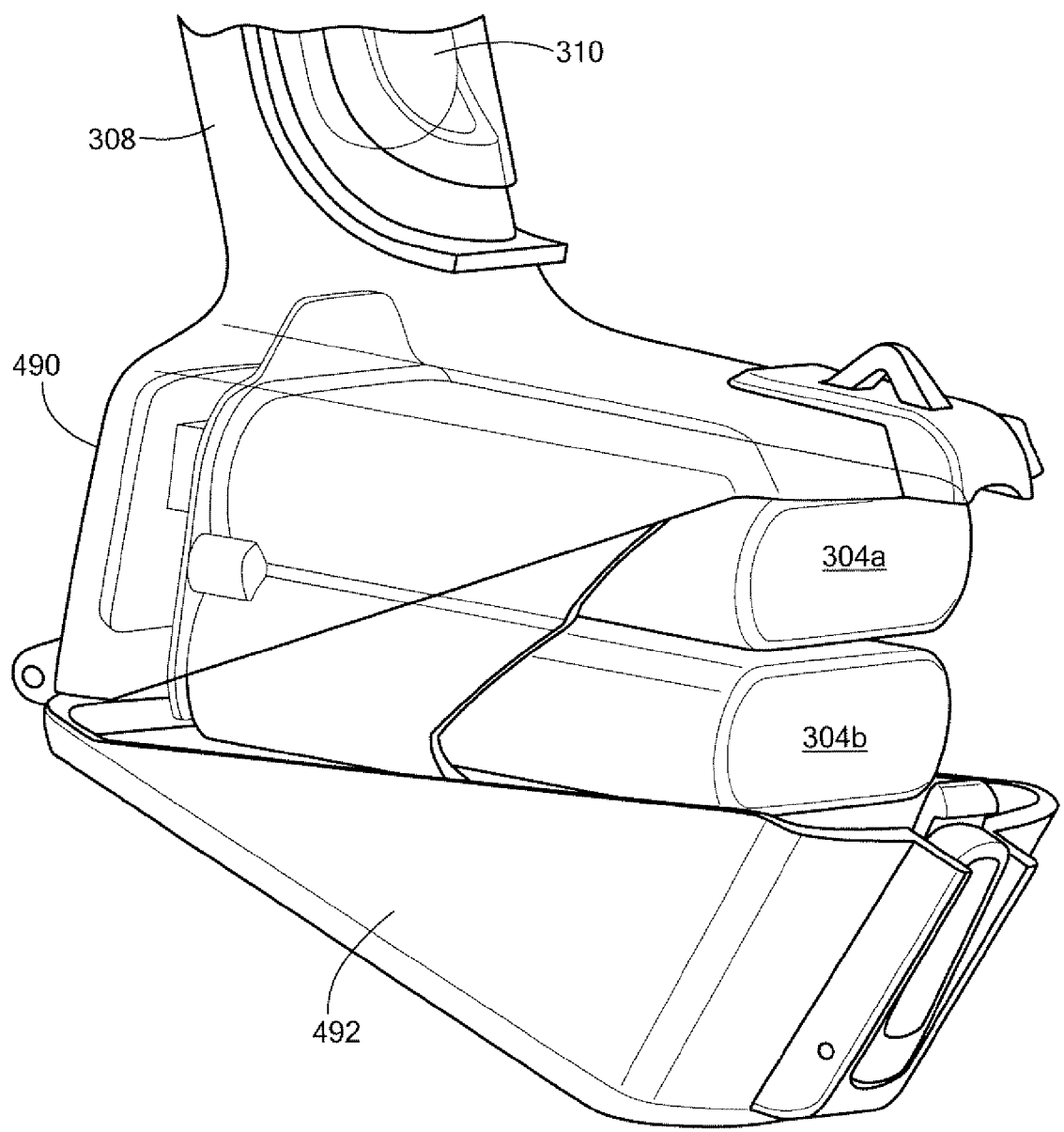
FIG. 29 is a schematic view showing the bottom of the handheld LIBS spectrometer handle with a pair of batteries removable therefrom.

FIG. 29 shows batteries 304a and 304b in handle 308 base 490 within cover 492 allowing replacement of the batteries. The batteries can also be recharged while residing in base 490 using known recharging receptacle designs and the like.

Figure 30:
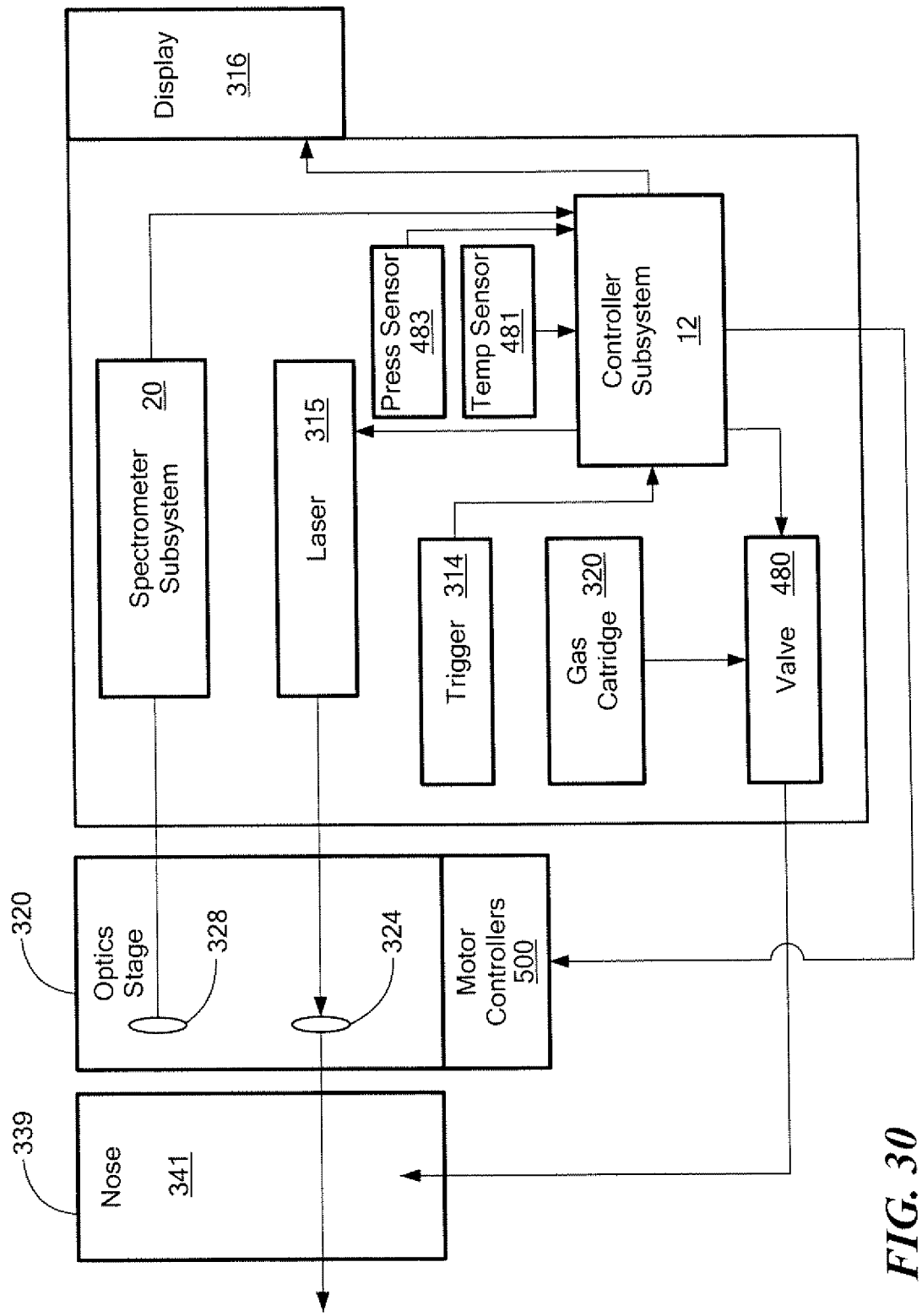
FIG. 30 is a block diagram showing the primary components associated with one preferred handheld LIBS spectrometer system in accordance with the invention.

The controller subsystem 12, FIG. 30 is configured to control laser 315, valve 480, motor controllers 500 for optics stage 320, and display 316 based on, for example, signals output from spectrometer subsystem 20 and trigger 314.

Preferably, controller subsystem 12 controls motor controllers 500 to move optic stage and thus laser focusing lens 324 (and detection lens 328) forward and rearward to create a small (e.g., 5µ-100µ) spot size focused automatically by reading the output of spectrometer subsystem 20 as the laser is automatically fired by controller subsystem 12 and by analyzing one or more element intensity peaks as discussed above with reference to FIGS. 4A-4C. Controller subsystem 12 may be configured to perform this autofocusing step as a part of initial testing and to determine and save the focusing lens location that yielded the maximum intensity for one or more elements. Controller subsystem 12 may further be configured to automatically trigger laser 315 to fire a number of cleaning shots to burn off material on the surface of the sample allowing underlying clean material to be analyzed. By controlling the movement of the optics stage, the cleaning shots are focused and can be directed to different portions of the sample. Controller subsystem 12 may be configured to automatically focus the laser beam by moving optics stage 320 to position the laser beam at a number of different areas on the sample and to automatically detect and terminate the cleaning shots to save battery power when the sample is sufficiently clean for analysis.

Controller subsystem 12 may further be configured to control laser 315 and optics stage 320 to move the laser beam among several different locations on the sample or target surface to enable an appropriate determination of sample homogeneity and to automatically stop the laser firing sequence to save battery power once it is determined that the appropriate spectra have been detected and/or the sample is homogeneous.

To detect certain elements, gas purging may be required and controller subsystem 12 controls valve 480 to provide purging gas to nose section 339. Preferably, only a small supply of purging gas is required in the purge system because one or more nozzles is configured to deliver a small spray of argon locally to the nose section purge chamber. Controller subsystem 12 may also control valve 480 as a function of the laser firing sequence to further limit purging gas use during analysis, cleaning, calibration, and the like as set forth above.

In some examples, a microprocessor(s), computer, application specific integrated circuit, field programmable gate array, computer server and client subsystem, or similar means is programmed as set forth herein. Other equivalent algorithms and computer code can be designed by software engineers and/or programmers skilled in the art using the specification provided herein.

Figure 31:
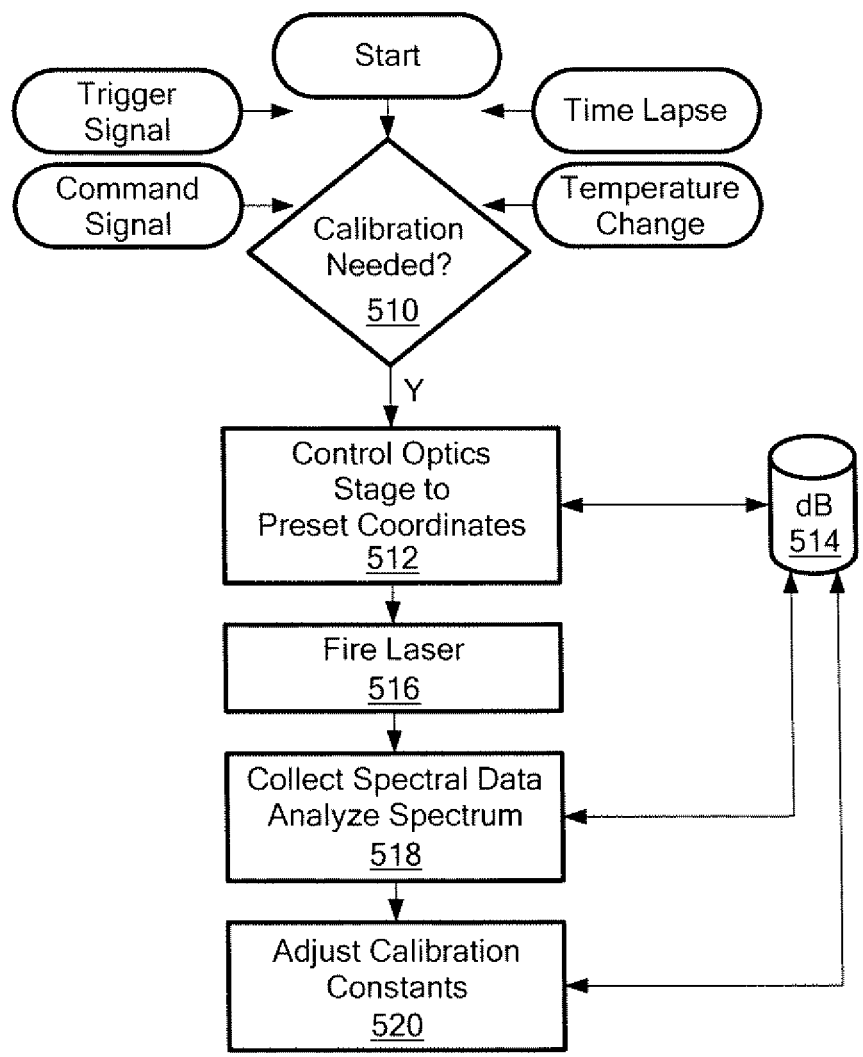
FIG. 31 is a flow chart depicting the primary steps of a calibration routine in accordance with a method of the invention and in accordance with computer instructions operating on the controller subsystem show in FIG. 30.

As shown in FIG. 31, the auto-calibration routine carried out by the computer instructions operating on controller subsystems 12, FIG. 30 includes instructions which first determine whether calibration is needed, step 510. Auto-calibration can be initiated based on a trigger signal generated by trigger 314, FIG. 30, based on a command signal (for example when the user uses display 316 to select "auto-calibrate"), by a lapse of time (e.g., one to two hours since the last calibration), by a temperature change (e.g., as detected by temperature sensor 481, FIG. 30), or based on other criteria.

If calibration is determined to necessary or desirable, the optics stage is controlled to move the optics head and laser beam to preset coordinates so the laser beam focuses on the calibration standard 341, FIG. 18 of end plate 340, step 512, FIG. 31. These calibration coordinates may be stored in a database 514 (in memory, for example such as a RAM, ROM, PROM, or the like).

The laser is then powered providing a laser beam forming a plasma at the calibration standard, step 516 and spectral data is collected via the spectrometers and the resulting spectrum is analyzed, step 518 again using equations, spectral libraries, and the like in database 514. If needed, due to temperature changes, aging of components of the system, spectral drift of a spectrometer, or the like, the stored intensity and/or wavelength calibration constants and/or calibration curves can be verified, adjusted, or changed, step 520 for more accurate analysis when the device is subsequently used to analyze a sample.

Figure 9:
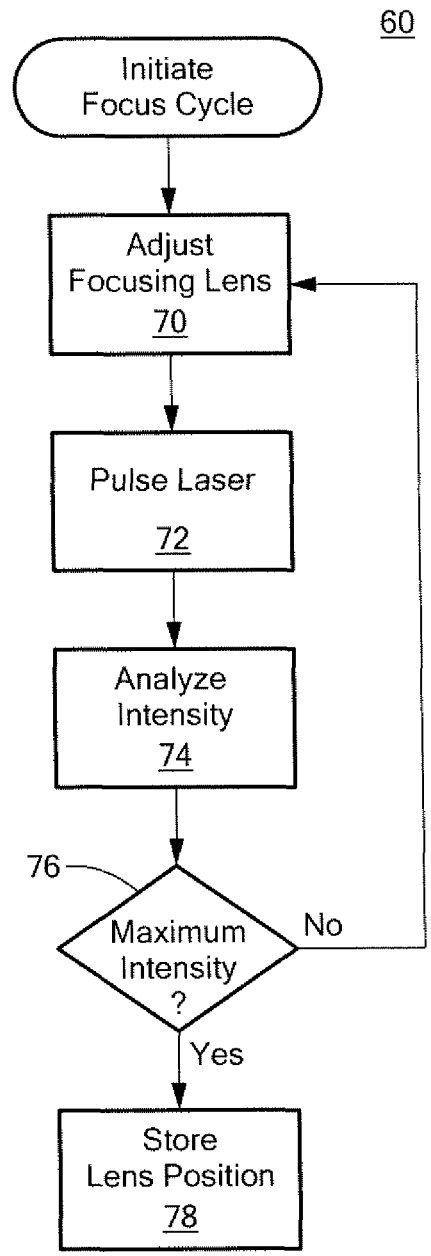
FIG. 9 is a flow chart depicting the primary steps associated with the focusing cycle depicted in FIG. 8.
Figure 32:
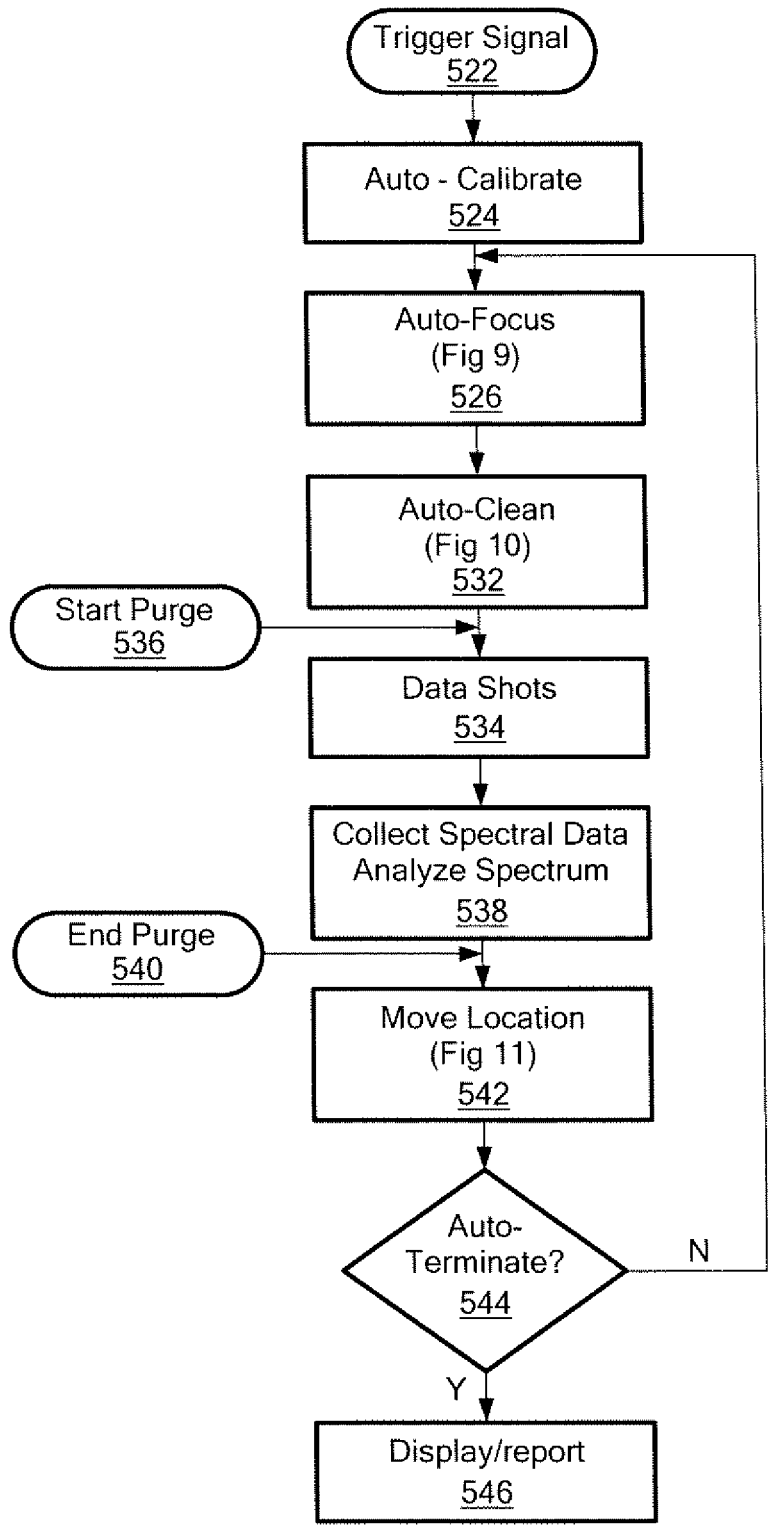
FIG. 32 is a flow chart depicting a method in accordance with the subject invention and also depicting the primary steps associated with computer instructions executed by the controller subsystem shown in FIG. 30.

In an analysis, the process typically begins when the unit is powered on and/or a trigger signal is received, step 522, FIG. 32. The auto-calibration routine of FIG. 31 may be carried out if necessary, step 524. If the temperature as sensed by the temperature sensor is within a specified range and a calibration has been carried out previously within a specified time limit, then auto-calibration is not needed. Then, the optics head is moved to produce a laser beam at one spot on the sample and the auto-focus routine of FIG. 9 is carried out, step 526, FIG. 32. Then, or concurrently with auto-focusing, cleaning shots may be generated using the auto-clean sequence depicted in FIG. 10, step 528, FIG. 32. In some examples, cleaning is effected by firing a predetermined number of laser pulses (e.g., 5-10). For the analysis or data shots after cleaning terminates, step 34, purging may begin as shown at 536. After each pulse of the laser, the spectral data of the resulting plasma is collected and analyzed (preferably using the adjusted calibration constants), step 538. Next, purging may terminate to conserve the purge gas as shown at 540 and the optics head is moved to produce a laser spot and to sample/test at a new location on the sample, step 542. The various locations may be pre-programmed.

Then, the auto-focus, auto-clean, data shots, and spectral analysis step may again be performed at the new location. Due to the optics stage, spots in a circle, square, cross, X, or other shape can be generated since the stage moves left and right and up and down relative to the sample. In some embodiments, at a new location, one or more cleaning shots may be performed first. If the intensity of the plasma detected is similar to the last spot, it may be assumed the laser beam is properly focused, so the auto-focusing steps may be skipped.

In some examples, this sequence terminates after a preset number of locations have been analyzed. In other examples, this sequence continues until it is determined the sample is homogeneous as shown in steps 94-100, FIG. 11. Pulling on the trigger may also terminate the testing. When the testing is complete as shown at 544, FIG. 32, the analysis results (elements present in the sample and concentrations of said elements) may be displayed on display 316, FIG. 17 and/or stored, step 546, FIG. 32.

Figure 33:
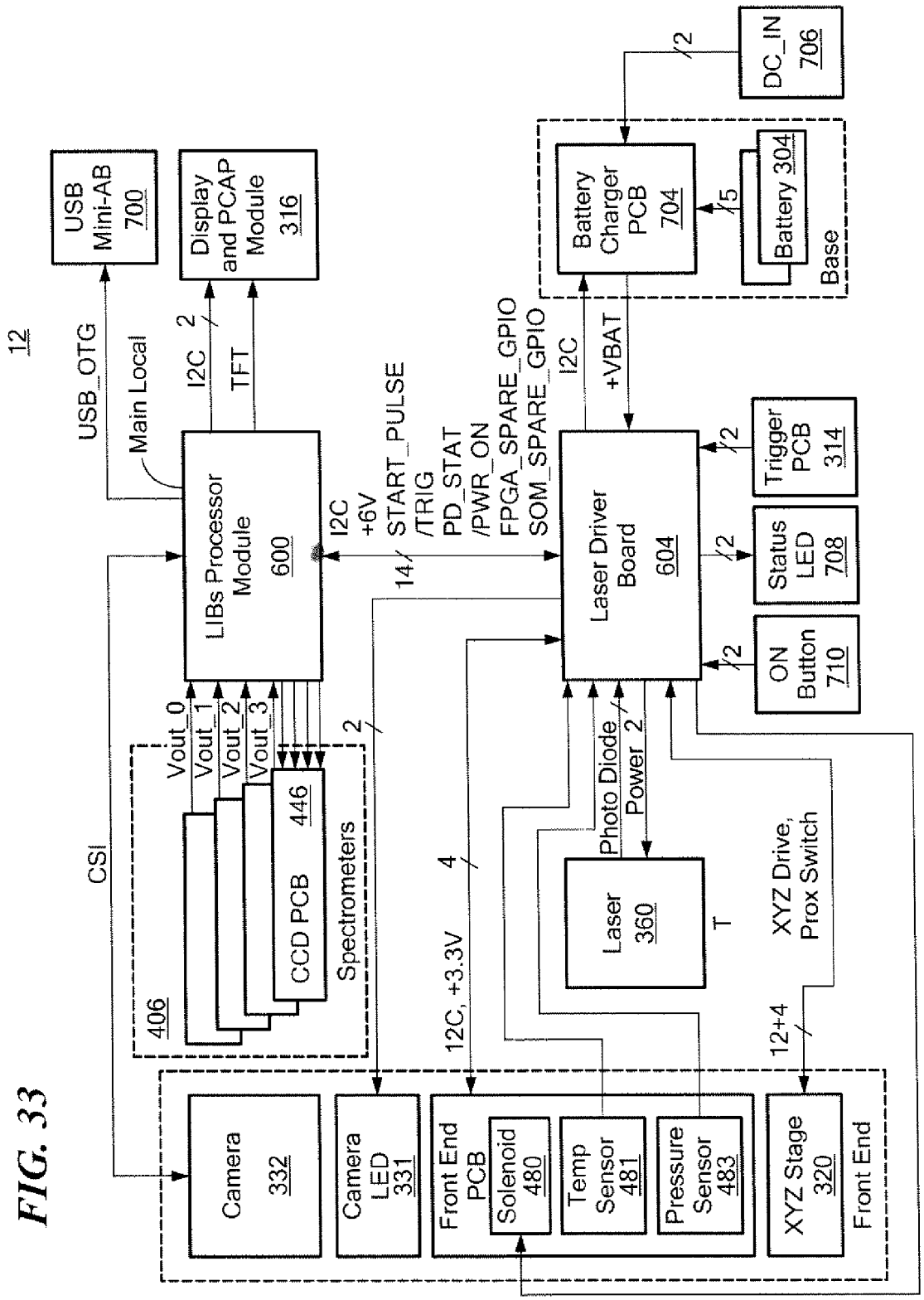
FIG. 33 is a block diagram showing an example of the primary electronic components associated with the controller subsystem of FIG. 30.
Figure 34:
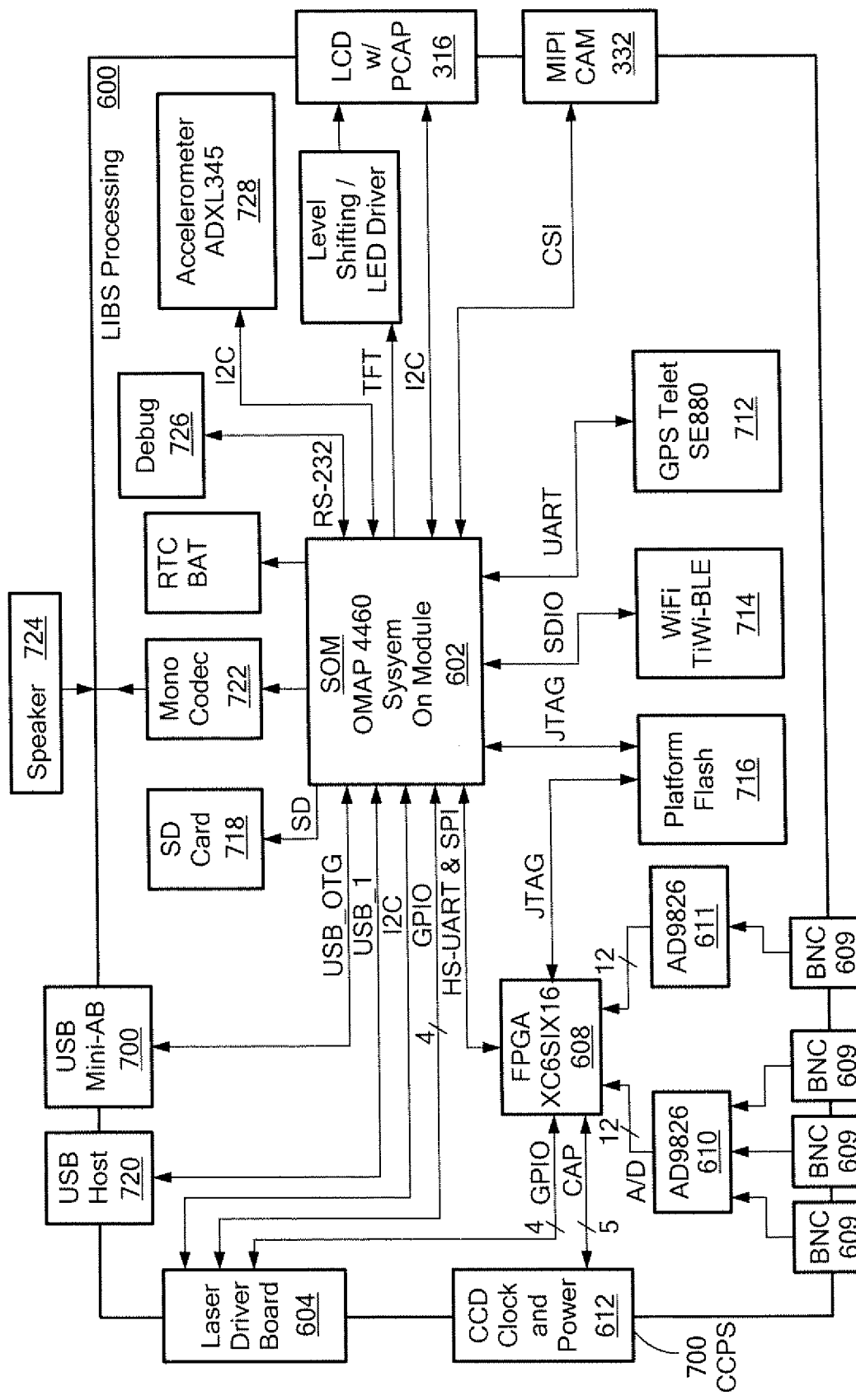
FIG. 34 is a block diagram showing an example of the primary electronic components associated with the processor module of FIG. 33.

FIG. 33 shows the primary electronic components of the system constituting the controller subsystem 12, FIG. 30. One printed circuit board 312, 313, FIG. 26 typically includes a LIBS processor module 600, FIG. 33, and the other printed circuit board includes laser driver board 604. LIBS processor module 600 is shown in FIG. 34 and includes or is embodied in a system on module card 602. Laser driver board 604, FIG. 33 includes microprocessor 620 and the other circuitry shown in FIG. 35.

Processor module 600 and laser driver board 604 may work together to control laser 360, FIG. 33, XYZ optics stage 320, solenoid 480, camera 332, and camera LED 331. Signals from the CCDs 446 of spectrometers 406 and camera 332 are typically provided to LIDS processor module 600 and processed thereby. Signals from temperature sensor 481 and pressure sensor 483 may be provided to laser driver board 604 and processed thereby.

In one example, a trigger signal from trigger 314 is provided to LIBS processor module 600 via laser driver board 604 and laser processor module 600 determines if battery power, the temperature of the unit, and/or other conditions allow firing the laser. If the laser is to be fired, LIBS processing module 600 signals laser driver board 604 to control the firing of laser 360 via the system on module card 602 FIG. 34 (e.g., an android processor module) and field programmable gate array (FPGA) 608.

Signals relating to electromagnetic radiation captured by the four CCDs 446 (FIG. 27) are delivered as shown at 609 to FPGA 608 via A/D converters 610 and 611 and to system on module 602. System on module 602 via FPGA 608 also controls CCD clocking and power as shown at 612. In this way, data collection between each firing of the laser is accomplished in an expedited manner.

When trigger 314, FIG. 33 is actuated, a signal is provided to laser driver board 608 which sends a signal to system on module 602, FIG. 34 located on laser processing module 600. System on module 602 sends signals to laser driver board 604 microprocessor 620, FIG. 35 which controls the motor drivers as shown at 630 to focus the laser beam to a new sample position. System on module 602 then issues a sequence of commands to FPGA 608 to perform a sequence of laser firing shots (for example 10). Data is collected from each resulting plasma between shots via output from the CCDs as shown at 609 in FIG. 34 provided to system on module 602 via FPGA 608 and then analyzed by system on module 602 for signal quality. Depending on any thresholds, system on module 602 may issue commands to FPGA 608 and microprocessor 620, FIG. 35 to collect further data from the same location on the sample. Or, system on module 602 may issue commands to move the laser beam to a new sample position and repeat the process described above.

Figure 35:
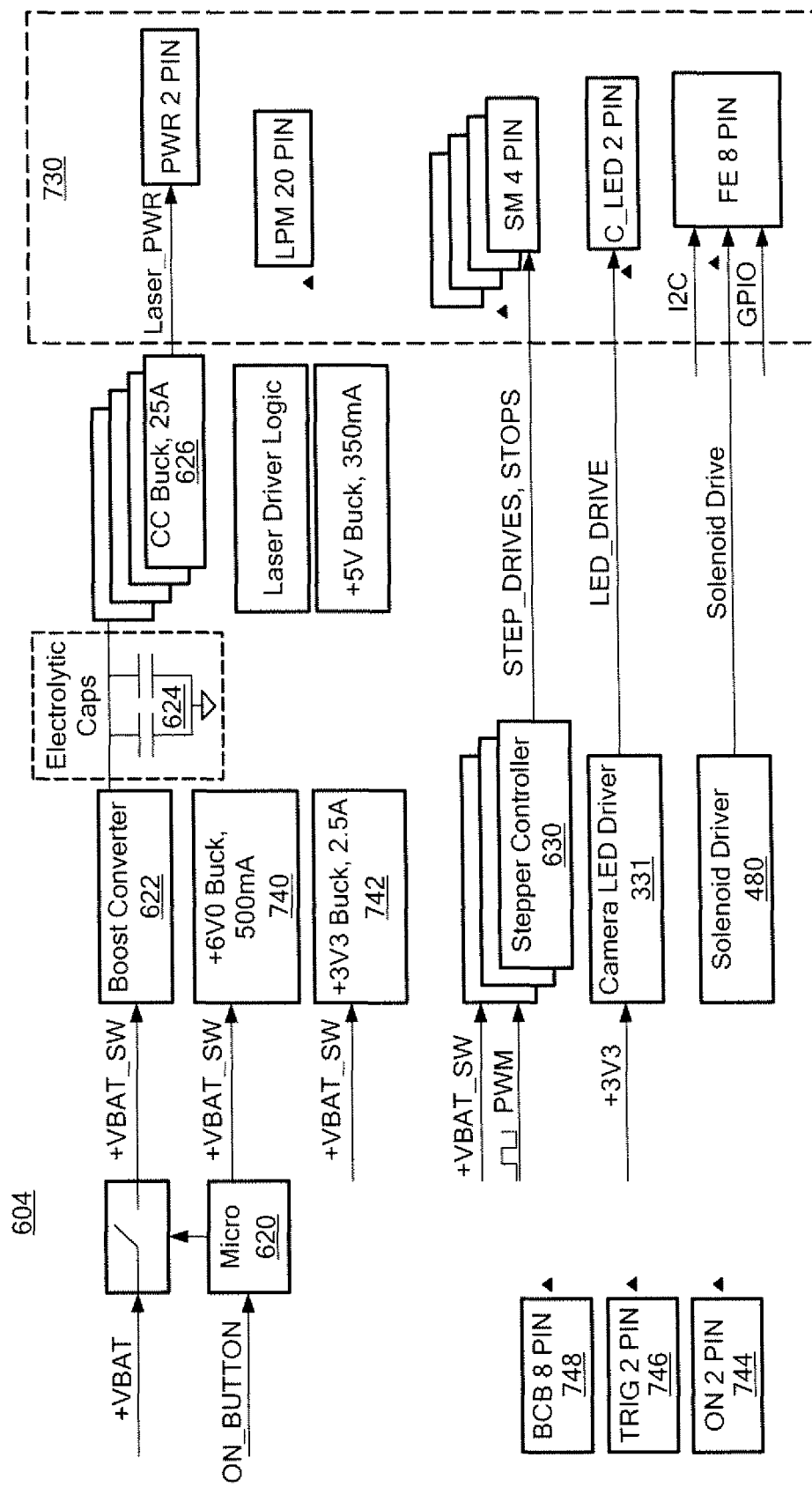
FIG. 35 is a block diagram showing an example of the primary electronic components of the laser driver board of FIG. 33.

Included within the laser firing sequences above, system on module 602 may issue commands to microprocessor 620, FIG. 35 of laser driver board 604 to command microprocessor 620 to measure the gas pressure as output from pressure sensor 483. If the gas pressure is above a preset threshold, microprocessor 620 may control solenoid 480 to begin gas purging prior to firing the laser 360 and to stop the flow of gas immediately after the last shot by controlling microprocessor 620 controlling solenoid driver 480. If adequate pressure is not sensed, system on module 602, FIG. 34 may display a message to display screen 316, FIG. 33 indicating the need to change out the gas cartridge.

During on measurement periods, system on module 602 is programmed to collect information from the laser driver board relating to battery charge, argon pressure, laser temperature, general internal temperature, and multiple internal power rail levels. If anything falls outside preset thresholds, appropriate actions can be taken such as flashing a battery level to warn the user that the batteries are low, on display 316, to prevent measurement if the laser is too hot, to prevent measurement if argon is in use and there is no argon left, and provide warnings if internal power rail voltages are outside acceptable ranges. The user may view the sample area on display screen 316 and record a picture with via on board camera 331.

Also shown in FIG. 33 is mini USB "on the go" connector 700, LCD display and touch screen 316, battery charger PCB 704 that controls battery charging with dual battery balancing during charging and discharging, status LED 708 located in the power button to indicate unit us powered up, and Power button 710, used to turn the unit on and off. FIG. 34 also depicts GPS module 712 for determining device location and communicating such information to module 602, and Wifi module 714 used to connect to and communicate with local WiFi networks.

Platform flash memory 716 is used to contain FPGA code that is loaded to the FPGA on power up. Flash 716 may be reprogrammed by the SOM 602 as needed. SD card 718 is used for saving collected data. USB Host port 720 is an extra port available as needed. Audio Monocodec 722 is used to convert SOM digital data into analog drive signals to the speaker 724. This can be used to announce material identification or other possible warnings to users. Serial "debug" port 726 is used at the factory for low level communication with the SOM 602. Accelerometer 728 can be used to determine instrument orientation so that the LCD display may be properly rotated and also used to record extreme shock experienced by the instrument.

FIG. 35 shows various connectors 730 from input arrows to named devices, six volt power supply 740 used by multiple sections on the board and off board, 3.3 volt power supply 742 used by multiple sections on the board and off board, connector 744 to the power on button, connector 746 to the trigger button, and 748 connector to the battery charger board.

Thus, although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant cannot be expected to describe certain insubstantial substitutes for any claim element amended.

Other embodiments will occur to those skilled in the art and are within the following claims. One example includes a Raman laser and Raman spectroscopy.

What is claimed is:

1. A handheld LIBS spectrometer comprising:
a housing;
an optics stage movably mounted to the housing and including an optics head with:
a laser focusing lens, and
a detection lens;
one or more motors configured to move the optics head left and right and move the optics head up and down and optionally advance and retract the optics head;
a laser source in the housing oriented to direct a laser beam directly to the laser focusing lens in the optics head;
a spectrometer subsystem in the housing configured to receive electromagnetic radiation from the detection lens and provide an output; and
a controller subsystem responsive to the output of the spectrometer subsystem and configured to control the laser source and said one or more motors to control said one or more motors to initiate a moving spot cycle and, at each location on the sample, to initiate an auto clean routine and perform a purge cycle.

2. The handheld LIBS spectrometer of claim 1 in which said optics stage further includes a camera with a camera lens.

3. The handheld LIBS spectrometer of claim 1 further including one or more rails attached to one of the optic stage and the housing and corresponding one or more linear bearings attached to the other of the optics stage and the housing.

4. The handheld LIBS spectrometer of claim 1 in which there are one or more motors attached to one of the optic stage and the housing driving the other of the optics stage and the housing for moving the optic stage relative to the housing.

5. The handheld LIBS spectrometer of claim 1 including a first frame member moveably coupled to the housing in a first direction, and a second frame member moveably coupled to the first frame member in a second direction and moveably coupled to the optics head in a third direction.

6. The handheld LIBS spectrometer of claim 5 including a first motor drive which drives the first frame member relative to the housing in the first direction,
a second motor drive which drives the second frame member relative to the first frame in the second direction, and
a third motor drive which drives the optics head relative to the second frame in the third direction.

7. The handheld LIBS spectrometer of claim 6 in which the first motor drive drives the first frame member and the optics head right and left.

8. The handheld LIBS spectrometer of claim 6 in which the second motor drive drives the second frame member and the optics head up and down.

9. The handheld LIBS spectrometer of claim 6 in which the third motor drive drives the optics head forward and rearward.

10. The handheld LIBS spectrometer of claim 1 in which said controller subsystem is configured to control said one or more motors to move the optics stage to initiate a calibration routine.

11. The handheld LIBS spectrometer of claim 10 in which said calibration routine includes computer instructions which control one or more motors to move said optics stage to a predetermined set of coordinates, to power the laser to produce a laser beam, to process the output of the spectrometer subsystem, and to calibrate the spectrometer.

12. The handheld LIBS spectrometer of claim 11 in which said computer instructions which calibrate the spectrometer include instructions which determine wavelength and/or intensity calibration constants based on the output of the spectrometer subsystem.

13. The handheld LIBS spectrometer of claim 1 in which the controller subsystem is configured to control said one or more motors to move said optics stage to initiate an auto-focus routine.

14. The handheld LIBS spectrometer of claim 1 in which said moving spot cycle includes computer instructions which control said one or more motors to move said optics stage to a plurality of locations and, at each location, to:
power the laser to produce a laser beam, and
process the output of the spectrometer subsystem.

15. The handheld LIBS spectrometer of claim 14 in which the controller subsystem is configured to initiate the auto-focus routine and the auto-clean routine at each said location.

16. The handheld LIBS spectrometer of claim 15 in which the controller subsystem is configured to initiate said purge cycle during said moving spot cycle.

17. The handheld LIBS spectrometer of claim 1 in which said laser source has an output wavelength of approximately 1.5μ.

18. The handheld LIBS spectrometer of claim 1 in which the laser source is a class one or class two laser.

19. The handheld LIBS spectrometer of claim 1 in which the laser focusing lens is configured to produce a laser spot size equal to or less than 100μ on a sample.

20. The handheld LIBS spectrometer of claim 1 in which the spectrometer subsystem includes a plurality of optical bundles optically coupled between said detection lens and a plurality of spectrometer enclosures.

21. The handheld LIBS spectrometer of claim 20 in which said spectrometer enclosures are coupled to each other in the housing.

22. The handheld LIBS spectrometer of claim 21 in which each spectrometer enclosure includes a floor and an open top, the floor of one enclosure configured to cover the open top of an adjacent enclosure.

23. The handheld LIBS spectrometer of claim 22 in which an outer spectrometer enclosure in the array includes a lid covering its open top.

24. The handheld LIBS spectrometer of claim 20 in which each spectrometer enclosure includes optical devices directing electromagnetic radiation from its optical bundle to a sensor.

25. The handheld LIBS spectrometer of claim 24 in which said sensor is a CCD sensor.

26. The handheld LIES spectrometer of claim 24 in which one or more said optical devices are adjustable with respect to the spectrometer enclosure.

27. The handheld LIBS spectrometer of claim 24 in which said optical devices include a grating with different spectrometer enclosures having different gratings and/or gratings at different angles.

28. The handheld LIBS spectrometer of claim 24 in which the optical devices of each spectrometer enclosure are in a Czerny-Turner configuration.

29. The handheld LIBS spectrometer of claim 1 further including a nose section forward of the optics stage and attached to the housing.

30. The handheld LIBS spectrometer of claim 29 in which the nose section includes an end plate with an aperture for the laser beam passing through the laser focusing lens.

31. The handheld LIBS spectrometer of claim 30 in which the nose section includes a shield spaced from the end plate defined defining a purge cavity between the shield and the end plate in front of the optics stage.

32. The handheld LIBS spectrometer of claim 31 in which the shield is made of fused silica for protecting the laser focusing lens and detection lens of the optic stage from plasma generated by the laser.

33. The handheld LIBS spectrometer of claim 31 further including a gas source fluidly coupled to the purge cavity.

34. The handheld LIBS spectrometer of claim 33 in which the housing includes a handle and the gas source includes a gas cartridge disposed in the housing.

35. The handheld LIBS spectrometer of claim 34 in which the gas cartridge is pivotably disposed in the housing handle.

36. The handheld LIBS spectrometer of claim 35 in which the gas source cartridge is fluidly coupled to the purge cavity via a regulator, the regulator is rotatably coupled to the housing, and the gas source cartridge is coupled to the rotating regulator.

37. The handheld LIBS spectrometer of claim 33 in which the gas source is fluidly connected to the purge cavity via a controllable valve.

38. The handheld LIBS spectrometer of claim 37 in which said controller subsystem is configured to automatically control said valve.

39. The handheld LIBS spectrometer of claim 29 in which said nose section includes a calibration standard for self-calibrating the spectrometer when controller subsystem controls the optic stage to orient the laser focusing lens to focus laser energy on the calibration standard of the nose section.

40. A handheld LIBS spectrometer comprising:
a housing;
an optics stage movably mounted to the housing via one or more motors;
a laser source in the housing oriented to direct a laser beam to the optics stage;
a spectrometer subsystem in the housing configured to receive electromagnetic radiation from the optics stage and provide an output, the spectrometer subsystem including a plurality of spectrometer enclosures; and
a controller subsystem responsive to the output of the spectrometer subsystem and configured to control the laser source and said one or more motors to control said one or more motors to initiate a moving spot cycle and, at each location on the sample, to initiate an auto clean routine and perform a purge cycle.

41. The handheld LIBS spectrometer of claim 40 in which the optics stage moveably mounted to the housing includes an optical head with a laser focusing lens and a detection lens and the optics stage includes one or more motors are configured to advance and retract the optical head, move the optical head left and right, and/or move the optical head up and down.

42. The handheld LIBS spectrometer of claim 41 in which the laser focusing lens is configured to produce a laser spot size equal to or less than 100μ on a sample.

43. The handheld LIBS spectrometer of claim 40 in which the controller subsystem is configured to control said one or more motors to move said optical head to initiate an auto-focus routine.

44. The handheld LIBS spectrometer of claim 43 in which said moving spot cycle includes computer instructions which control said one or more motors to move said optical head to a plurality of locations and at each location to:
power the laser to produce a laser beam, and
process the output of the spectrometer subsystem.

45. The handheld LIBS spectrometer of claim 44 in which the controller subsystem is configured to initiate the auto-focus routine and the auto-clean routine at each said location.

46. The handheld LIBS spectrometer of claim 45 in which the controller subsystem is configured to initiate said purge cycle during said moving spot cycle.

47. The handheld LIBS spectrometer of claim 40 in which said laser source has an output wavelength of approximately 1.5μ.

48. The handheld LIBS spectrometer of claim 40 in which the laser source is a class one or class two laser.

49. The handheld LIBS spectrometer of claim 40 in which the spectrometer subsystem includes a plurality of optical bundles optically coupled between said optics stage and the plurality of spectrometer enclosures.

50. The handheld LIBS spectrometer of claim 40 in which said spectrometer enclosures are coupled to each other in the housing.

51. The handheld LIBS spectrometer of claim 50 in which each spectrometer enclosure includes a floor and an open top, the floor of one enclosure configured to cover the open top of an adjacent enclosure.

52. The handheld LIBS spectrometer of claim 51 in which an outer spectrometer enclosure in the array includes a lid covering its open top.

53. The handheld LIBS spectrometer of claim 51 in which each spectrometer enclosure includes optical devices directing electromagnetic radiation from its optical bundle to a sensor.

54. The handheld LIBS spectrometer of claim 53 in which said sensor is a CCD sensor.

55. The handheld LIBS spectrometer of claim 53 in which one or more said optical devices are adjustable with respect to the spectrometer enclosure.

56. The handheld LIBS spectrometer of claim 53 in which said optical devices include a grating with different spectrometer enclosures having different gratings and/or gratings at different angles.

57. The handheld LIBS spectrometer of claim 53 in which the optical devices of each spectrometer enclosure are in a Czerny-Turner configuration.

58. A handheld LIBS spectrometer comprising:
a housing;
an optics stage movably mounted to the housing via one or more motors including an optics head with a laser focusing lens and a detection lens;
a laser source in the housing oriented to direct a laser beam to the laser focusing lens;
a spectrometer subsystem in the housing configured to receive electromagnetic radiation from the detection lens and provide an output;
a nose section including an end plate and a shield spaced from the end plate and in front of the optics head defining a purge cavity between the shield and the end plate; and
a controller subsystem responsive to the output of the spectrometer subsystem and configured to control the laser source and said one or more motors to control said one or more motors to initiate a moving spot cycle and, at each location on the sample, to initiate an auto clean routine and perform a purge cycle.

59. The handheld LIBS spectrometer of claim 58 in which said end plate includes an aperture for the laser beam.

60. The handheld LIBS spectrometer of claim 58 in which the end plate is made of or includes a portion made of a calibration standard.

61. The handheld LIBS spectrometer of claim 60 further including a controller subsystem configured to automatically control said valve.

62. The handheld LIBS spectrometer of claim 58 further including a gas source fluidly coupled to the purge cavity.

63. The handheld LIBS spectrometer of claim 62 in which the housing includes a handle and the gas source includes a gas cartridge disposed in the housing.

64. The handheld LIBS spectrometer of claim 63 in which the gas cartridge is pivotably disposed in the housing handle.

65. The handheld LIBS spectrometer of claim 64 in which the gas source cartridge is fluidly coupled to the purge cavity via a regulator, the regulator is rotatably coupled to the housing, and the gas source cartridge is coupled to the rotating regulator.

66. The handheld LIBS spectrometer of claim 62 in which the gas source is fluidly connected to the purge cavity via a controllable valve.

67. The handheld LIBS spectrometer of claim 58 in which said controller subsystem is configured to control the optics stage to initiate a calibration routine.

68. The handheld LIBS spectrometer of claim 67 in which said calibration routine includes computer instructions which move said optics head to aim the laser beam at the calibration standard, to power the laser to produce a laser beam, to process the output of the spectrometer subsystem, and to calibrate the spectrometer.

69. The handheld LIBS spectrometer of claim 68 in which said computer instructions which calibrate the spectrometer include instructions which determine wavelength and/or intensity calibration constants based on the output of the spectrometer subsystem.

70. A method of analyzing a sample using a handheld LIBS spectrometer, the method comprising:
   powering a laser to produce a laser beam spot on a sample;
   initiating an auto-focus cycle to focus the spot on the sample;
   initiating an auto-clean cycle to clean multiple locations on the sample;
   initiating a moving spot cycle to analyze the sample; and
   at each location on the sample, initiating the auto-clean cycle and performing a purge cycle.

71. The method of claim 70 in which initiating the auto-focus cycle includes retracting and advancing a laser focusing lens, powering the laser, and analyzing a spectrum until the spectrum indicates a maximum or near maximum intensity resulting from a laser output focused to a spot on the sample.

72. The method of claim 70 in which the auto-clean cycle includes powering the laser, analyzing a spectrum, and moving the laser beam about the sample until the spectrum output stabilizes.

73. The method of claim 72 in which the auto-clean cycle automatically terminates when a rolling average of at least one peak intensity changes by less than a predetermined percentage.

74. The method of claim 70 in which during the moving spot cycle the laser is powered, a spectrum data is analyzed, and the laser beam spot on the sample is moved.

75. The method of claim 70 further including automatically initiating an auto-calibration cycle.

76. The method of claim 75 in which during the auto-calibration cycle the laser beam is aimed at a calibration standard, the laser is powered to produce a laser beam focused at the standard, a spectrometer output is analyzed, and calibration constants are determined.

77. The method of claim 76 in which the calibration standard is a component of the handheld LIBS spectrometer.

* * * * *